(12) United States Patent
Feng et al.

(10) Patent No.: US 11,668,593 B2
(45) Date of Patent: Jun. 6, 2023

(54) ESTIMATING PHASE FRACTION/DISTRIBUTION WITH DIELECTRIC CONTRAST ANALYSIS

(71) Applicant: ExxonMobil Technology and Engineering Company, Annandale, NJ (US)

(72) Inventors: Lang Feng, New York, NY (US); Stefan S. Natu, Jersey City, NJ (US); John J. Valenza, II, Pennington, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 594 days.

(21) Appl. No.: 16/248,973

(22) Filed: Jan. 16, 2019

(65) Prior Publication Data

US 2019/0242733 A1    Aug. 8, 2019

Related U.S. Application Data

(60) Provisional application No. 62/626,742, filed on Feb. 6, 2018.

(51) Int. Cl.
*G01F 1/66* (2022.01)
*G01F 1/74* (2006.01)
(Continued)

(52) U.S. Cl.
CPC ............. *G01F 1/66* (2013.01); *G01F 1/74* (2013.01); *G01N 22/00* (2013.01); *G01N 27/26* (2013.01);
(Continued)

(58) Field of Classification Search
CPC .. G01F 1/66; G01F 1/74; G01N 22/00; G01N 33/2823; G01N 21/85
See application file for complete search history.

(56) References Cited

U.S. PATENT DOCUMENTS

| | | | |
|---|---|---|---|
| 5,101,163 A | 3/1992 | Agar | |
| 5,298,903 A * | 3/1994 | Janos | ..................... H01Q 17/00 342/4 |

(Continued)

FOREIGN PATENT DOCUMENTS

WO    2010/069307 A1    6/2010

OTHER PUBLICATIONS

The International Search Report and Written Opinion of PCT/US2019/013746 dated May 7, 2019.
(Continued)

*Primary Examiner* — Alexander Satanovsky
*Assistant Examiner* — Lynda Dinh
(74) *Attorney, Agent, or Firm* — Vorys, Safer, Seymour and Pease LLP

(57) ABSTRACT

Methods and apparatus for examining a material are provided. One example method generally includes disposing the material in a dielectric contrast analysis structure, wherein the dielectric contrast analysis structure comprises a bulk dielectric substance and a plurality of receptacles in the bulk dielectric substance, wherein the material is disposed in one or more of the plurality of receptacles; exposing the dielectric contrast analysis structure to incident electromagnetic radiation; detecting resultant radiation from the exposed dielectric contrast analysis structure; and analyzing the detected resultant radiation to estimate at least one of a phase fraction and a phase distribution in the material. One example system generally includes an electromagnetic radiation source; a dielectric contrast analysis structure
(Continued)

comprising a bulk dielectric substance and a plurality of receptacles in the bulk dielectric substance for receiving the material; and an electromagnetic radiation detector, wherein the analysis structure is between the radiation source and the detector.

22 Claims, 16 Drawing Sheets

(51) Int. Cl.
  *G01N 22/00* (2006.01)
  *G01N 33/28* (2006.01)
  *G01N 21/85* (2006.01)
  *G01N 27/26* (2006.01)
  *G01N 21/41* (2006.01)

(52) U.S. Cl.
  CPC ......... *G01N 33/2823* (2013.01); *G01N 21/85* (2013.01); *G01N 2021/4173* (2013.01)

(56) References Cited

U.S. PATENT DOCUMENTS

| | | | | |
|---|---|---|---|---|
| 5,623,429 | A * | 4/1997 | Fortune | G09B 23/181 |
| | | | | 455/67.16 |
| 5,955,749 | A * | 9/1999 | Joannopoulos | B82Y 20/00 |
| | | | | 257/98 |
| 6,693,605 | B1 * | 2/2004 | Crouch | H01Q 15/24 |
| | | | | 343/909 |
| 7,679,374 | B2 | 3/2010 | Bromberg et al. | |
| 7,822,147 | B2 * | 10/2010 | Huang | H04L 27/364 |
| | | | | 375/296 |
| 8,855,947 | B2 | 10/2014 | Sheila-Vadde et al. | |
| 9,207,357 | B2 | 12/2015 | Steinhardt et al. | |
| 9,207,400 | B2 | 12/2015 | Ouyang et al. | |
| 2004/0125449 | A1 * | 7/2004 | Sales | G02B 5/3058 |
| | | | | 359/485.05 |
| 2009/0079976 | A1 | 3/2009 | Cunningham et al. | |
| 2011/0147073 | A1 * | 6/2011 | Kume | B82Y 25/00 |
| | | | | 174/391 |
| 2011/0267074 | A1 | 11/2011 | Xie et al. | |
| 2014/0252250 | A1 | 9/2014 | Botto et al. | |
| 2016/0161425 | A1 * | 6/2016 | Berezin | G01N 22/00 |
| | | | | 324/638 |
| 2019/0128993 | A1 * | 5/2019 | Hiller | G01S 3/48 |

OTHER PUBLICATIONS

Falcone, "Key Multiphase Flow Metering Techniques", Developments in Petroleum Science, 2009, 54, pp. 47-109.

Man et al., "Phontonic Band Gap in Isotropic Hyperuniform Disordered Solids With Low Dielectric Contract", Optic Express, 2013, 21, pp. 19972-19981.

* cited by examiner

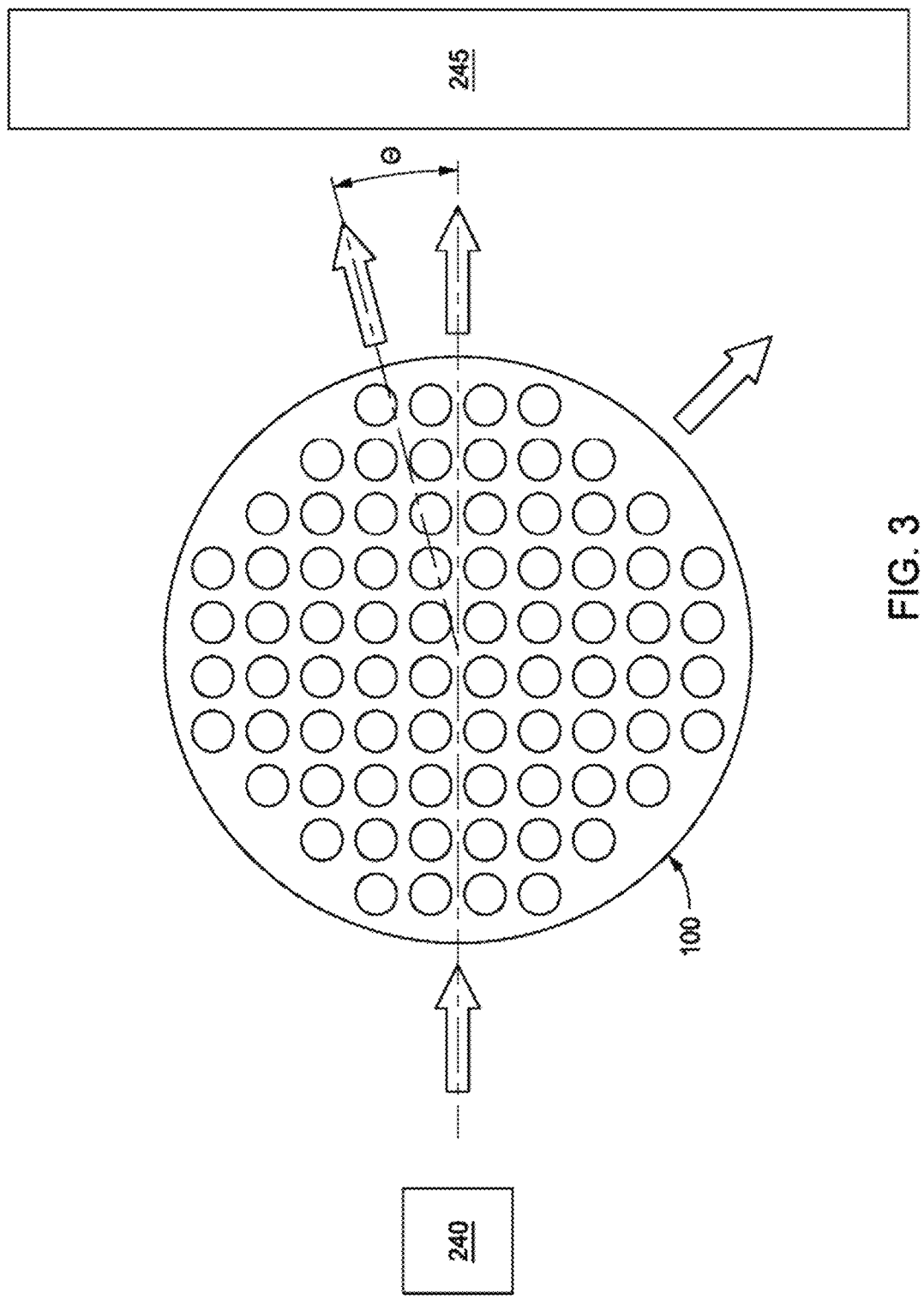

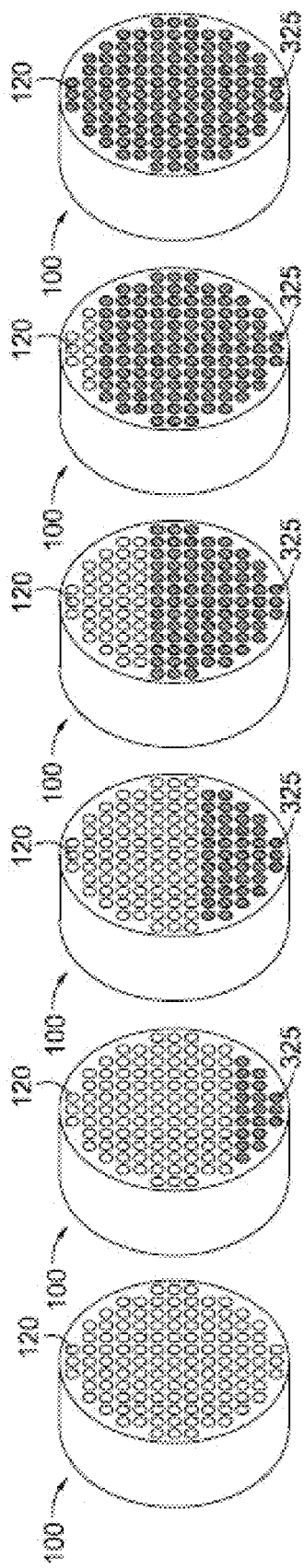
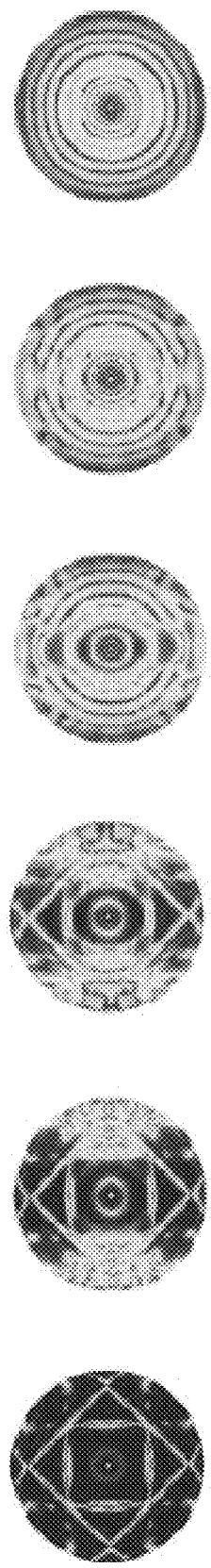
FIG. 8A FIG. 8B FIG. 8C FIG. 8D FIG. 8E FIG. 8F
FIG. 9A FIG. 9B FIG. 9C FIG. 9D FIG. 9E FIG. 9F

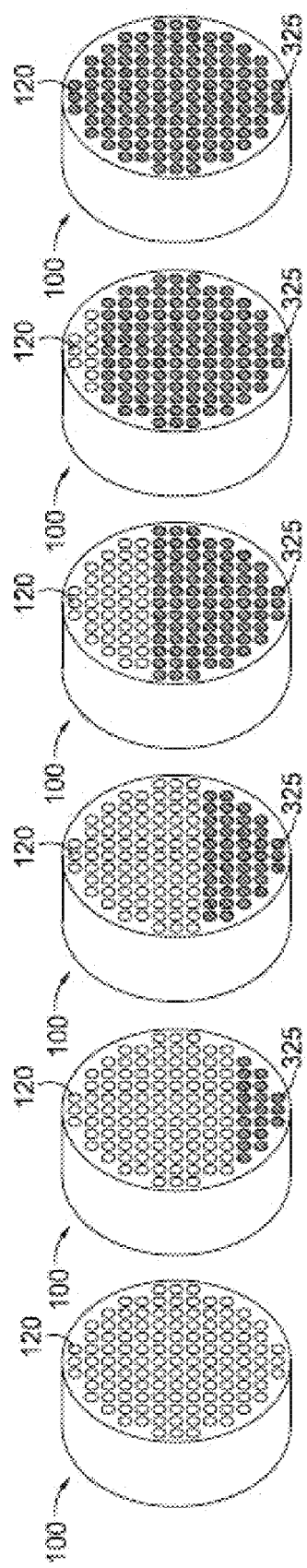

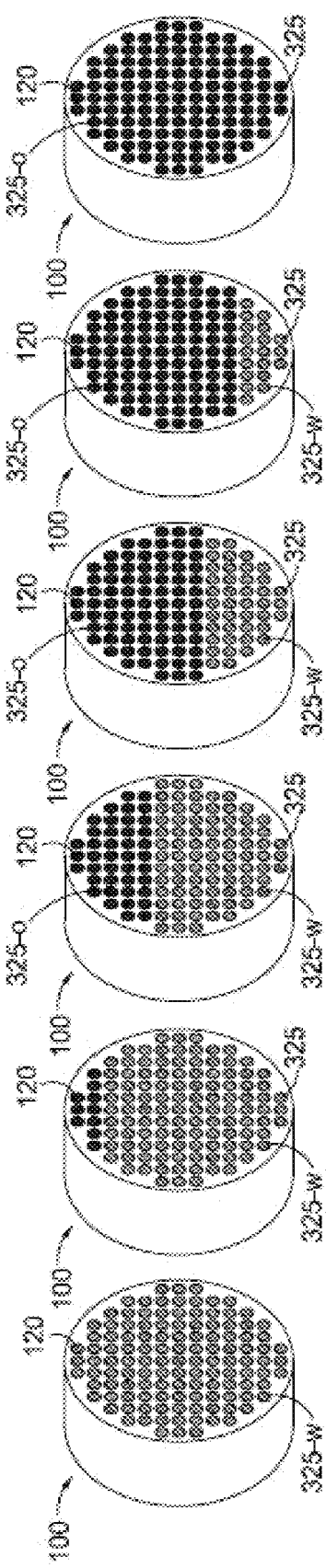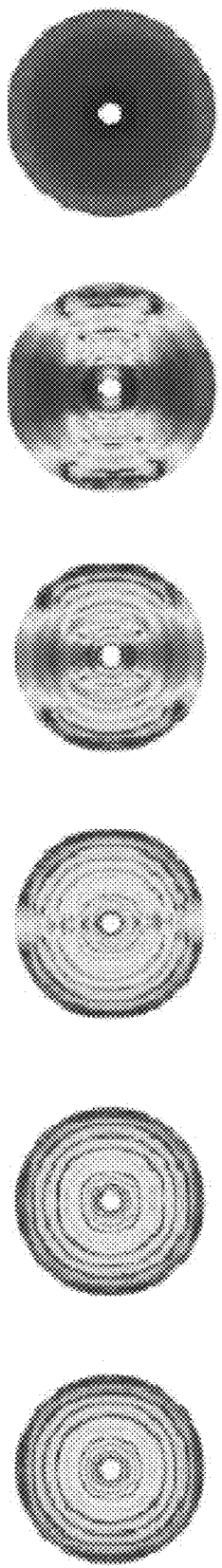

ESTIMATING PHASE FRACTION/DISTRIBUTION WITH DIELECTRIC CONTRAST ANALYSIS

CROSS-REFERENCE TO RELATED APPLICATIONS

This application claims priority to U.S. Provisional Application Ser. No. 62/626,742 filed Feb. 6, 2018, which is herein incorporated by reference in its entirety.

FIELD

This disclosure relates generally to the field of hydrocarbon management. Specifically, exemplary embodiments relate to equipment and methods for examining materials related to hydrocarbon prospecting, discovery, extraction, production, transportation, and/or refinement, with dielectric contrast analysis.

BACKGROUND

This section is intended to introduce various aspects of the art, which may be associated with exemplary embodiments of the present disclosure. This discussion is believed to assist in providing a framework to facilitate a better understanding of particular aspects of the present disclosure. Accordingly, it should be understood that this section should be read in this light, and not necessarily as admissions of prior art.

During operations related to hydrocarbon prospecting, production, and/or refinement, material, such as production fluid produced from a reservoir via a wellbore, will be examined. Production "fluid" may, in fact, contain multiple substances in multiple physical states. For example, production fluid may include liquid hydrocarbons, liquid water, natural gas, and various particulates, such as sand or wax. The production fluid will be examined to estimate quantities, such as the fraction of water, and/or the fraction of hydrocarbon in gas state (as opposed to liquid state). The flow of the production fluid may also be examined to estimate quantities, such as the flow rate of the bulk production fluid, and/or the flow rate of the water phase of the bulk production fluid.

Conventionally, multiphase flow meters deploy more than one technology to independently measure the substance fraction and distribution as well as the flow rate of the substances. The technologies used for measuring substance fraction and distribution include Electrical Impedance Tomography ("EIT"), Electrical Capacitance Volume Tomography ("ECVT"), wire mesh sensor, microwave sensor, Nuclear Magnetic Resonance ("NMR"), and radiography and tomography with radioactive source (e.g., Gamma Ray tomography). Microwave-based flow meters have been used to examine materials related to hydrocarbon prospecting, production, and/or refinement. For example, microwave transmission is routinely used in multiphase flow measurement. Microwave-based flow meters may infer dielectric constant information by measuring attenuation and time delay of microwave signals between two or more antennas. This information only reflects effective composite properties through the use of effective medium theories. These microwave-based flow meters do not indicate flow morphology, or work well at high water fraction. Furthermore, they are typically unreliable in the presence of gas, which is typical in many production environments. Other conventional microwave-based technologies may place microwave antennas across a dielectric monolith to detect a shift in resonant frequency due to the deposition of a new phase, such as conductive soot. These methods only work at low soot concentration, and do not elucidate the distribution of soot in the monolith.

Other techniques for morphology measurement include Gamma Ray Tomography. However, this technique can be costly and may be subject to substantial regulatory challenges associated with radioactive sources.

In the field of optics, guiding and splitting electromagnetic waves with dielectric structures is practiced, often with dielectric structures having symmetry or other designs. However these dielectric structures are designed and produced with the goal of manipulating the electromagnetic waves. The material make-up of the dielectric structure is fixed, not being subject to examination.

More efficient equipment and techniques to evaluate fraction and/or spatial distribution of various phases of material related to hydrocarbon management would be beneficial.

SUMMARY

In an embodiment, a method of examining a material includes disposing the material in a dielectric contrast analysis structure, wherein the dielectric contrast analysis structure includes a bulk dielectric substance; and a plurality of receptacles in the bulk dielectric substance, wherein the material is disposed in one or more of the plurality of receptacles; exposing the dielectric contrast analysis structure to incident electromagnetic radiation; detecting resultant electromagnetic radiation from the exposed dielectric contrast analysis structure; and analyzing the detected resultant electromagnetic radiation to estimate at least one of a phase fraction and a phase distribution in the material.

In an embodiment, a system for examining a material includes one or more electromagnetic radiation sources; a dielectric contrast analysis structure including a bulk dielectric substance; and a plurality of receptacles in the bulk dielectric substance for receiving the material; and one or more electromagnetic radiation detectors, wherein the dielectric contrast analysis structure is between the electromagnetic radiation source and the electromagnetic radiation detector.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

FIG. 3 illustrates a convention for referencing the angle at which resultant electromagnetic radiation exits the dielectric contrast analysis structure of FIG. 1.

FIGS. 8A-8F illustrate an example of different amounts of material to be examined in receptacles of the dielectric contrast analysis structure of FIG. 1.

FIGS. 9A-9F illustrate polar intensity plots of the transmission coefficients from the dielectric contrast analysis structures of FIGS. 8A-8F, respectively.

FIGS. 10A-10F illustrate another example of different amounts of material to be examined in receptacles of the dielectric contrast analysis structure of FIG. 1.

FIGS. 11A-11F illustrate polar intensity plots of the transmission coefficients from the dielectric contrast analysis structures of FIGS. 10A-10F, respectively.

FIGS. 12A-12F illustrate different amounts and types of material to be examined in receptacles of the dielectric contrast analysis structure of FIG. 1.

FIGS. 13A-13F illustrate polar intensity plots of the transmission coefficients from the dielectric contrast analysis structures of FIGS. 12A-12F, respectively.

DETAILED DESCRIPTION

Figure 1:
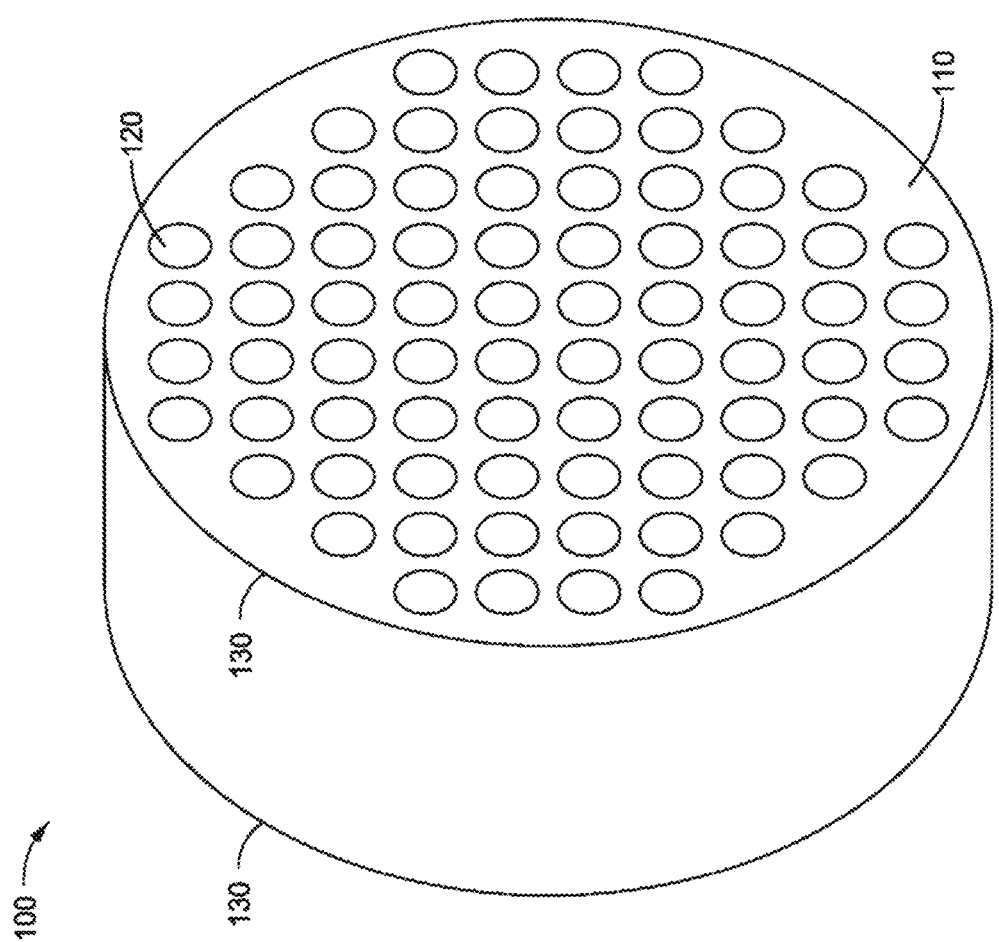
FIG. 1 illustrates an example of the dielectric contrast analysis structure, according to embodiments disclosed herein.

It is to be understood that the present disclosure is not limited to particular devices or methods, which may, of course, vary. It is also to be understood that the terminology used herein is for the purpose of describing particular embodiments only, and is not intended to be limiting. As used herein, the singular forms "a", "an," and "the" include singular and plural referents unless the content clearly dictates otherwise. Furthermore, the words "can" and "may" are used throughout this application in a permissive sense (i.e., having the potential to, being able to), not in a mandatory sense (i.e., must). The term "include," and derivations thereof, mean "including, but not limited to." The term "coupled" means directly or indirectly connected. The word "exemplary" is used herein to mean "serving as an example, instance, or illustration." Any aspect described herein as "exemplary" is not necessarily to be construed as preferred or advantageous over other aspects. The term "uniform" means substantially equal for each sub-element, within about 10% variation. The term "nominal" means as planned or designed in the absence of unplanned phenomena. "Nominal" may be implied as commonly used in fields related to hydrocarbon management.

As used herein, the term "state" generally refers to the physical state of a material, such as solid, liquid, or gas. "Phase" shall refer to the state, composition, and/or nature (identifiably distinct form) of a material. "Substance" shall refer to a mono-phasic material.

"Obtaining" data shall mean any method or combination of methods of acquiring, collecting, or accessing data, including, for example, directly measuring or sensing a physical property, receiving transmitted data, selecting data from a group of physical sensors, identifying data in a data record, and retrieving data from one or more data libraries.

The term "near-real time" refers to the time delay resulting from detecting, sensing, collecting, filtering, amplifying, modulating, processing, and/or transmitting relevant data or attributes from one point (e.g., an event detection/sensing location) to another (e.g., a data monitoring location). In some situations, a time delay from detection of a physical event to observance of the data representing the physical event is insignificant or imperceptible, such that near-real time approximates real time. Near-real time also refers to longer time delays that are still short enough to allow timely use of the data to monitor, control, adjust, or otherwise impact subsequent detections of such physical events.

As used herein, "hydrocarbon management" includes hydrocarbon extraction, hydrocarbon production, hydrocarbon exploration, hydrocarbon transportation, hydrocarbon storage, hydrocarbon refining, hydrocarbon characterization, and processing, identifying potential hydrocarbon resources, identifying well locations, determining well injection and/or extraction rates, identifying reservoir connectivity, identifying qualities and quantities of fluids in place in reservoir, acquiring, disposing of, and/or abandoning hydrocarbon resources, reviewing prior hydrocarbon management decisions, and any other hydrocarbon-related acts or activities.

If there is any conflict in the usages of a word or term in this specification and one or more patent or other documents that may be incorporated herein by reference, the definitions that are consistent with this specification should be adopted for the purposes of understanding this disclosure.

This disclosure provides equipment and methods to measure/infer fraction and/or spatial distribution of various phases of matter with dielectric contrast using electromagnetic waves. For example, some embodiments involve measuring the anisotropic transmission of electromagnetic energy to infer substance fraction and/or spatial distribution. Embodiments may be used to uncover oil/water/gas/sand phase fractions and flow morphologies in multiphase flow (e.g., in a wellbore or pipeline).

One of the many potential advantages of the embodiments of the present disclosure is that the measurement device may be incorporated into steel pipe for measuring oil/water/gas/sand phase fractions and identifying flow morphologies. Compared to current multiphase flow meters, embodiments of the present disclosure may be capable of operating at lower power. For example, measurements may be made utilizing antennas operating at between about 0.01 mW and about 10.0 mW, or between about 0.1 mW and about 1.5 mW, or approximately 1.0 mW. This technology may find applications in digital oil field/process technology. As used herein the term "digital oil field" includes a broad range of technologies encompassing a wide varieties of measurement tools and workflows. The overarching objective is to improve the profitability of hydrocarbon production operations over a wide range of time scales. Non-limiting examples of digital oil field technologies include autonomous control of operating facilities, data integration, decision support and automation, and production optimization. Production optimization, or near-real time production optimization includes but is not limited to optimizing the production of a single well, or multiple wells up to and including the production of an entire field of wells. Optimization is achieved by utilizing production data from one or multiple wells, and/or an entire field. The well data include but are not limited to pressure, pressure drop, temperature, flow regime, flow rates and phase fractions. Embodiments of the present disclosure can thereby be useful in the prospecting, discovery, extraction, production, processing, transportation, and/or refinements of hydrocarbons from subsurface formations. Benefits may also include improvement in cost, ease of deployment, and accuracy in multiphase flow measurements. Beneficially, this may significantly increase opportunities for intelligent monitoring and/or near-real time production optimization in digital oilfield applications.

Some embodiments disclosed herein exploit the physics of photonic crystals. In particular, the photonic band structure may be identified and/or associated with the anisotropic interaction of electromagnetic waves with a spatial distribution of various phases of matter with dielectric contrast. The photonic band structure may be altered by substituting material, such as oil or water, into this spatial distribution of matter. Some embodiments may detect this phase substitution in order to measure phase fractions and/or spatial distribution of the material. Some embodiments may be able to achieve electromagnetic wave transmission in the frequency band where high water fraction, even complete water saturation, would normally preclude the propagation of electromagnetic energy. Some embodiments may be able to elucidate distribution or flow morphologies by exploiting simple symmetry principles.

The material to be examined may include one or more substances, solutions, mixtures, dispersions, bubbles, particulates, colloids, vesicles, and/or emulsions, of a single physical state or of multiple states. For example, the material may be a single substance (e.g., $H_2O$) of a single state or multiple states (e.g., ice, water, steam). As another example, the material may be a solution with the solute material of the same state(s) as the solvent material. As another example, the material may be a mixture made up of two or more different materials which are mixed but are not combined chemically. As another example, the material may be a dispersion in which particles of a first material are dispersed in a continuous phase of a different material (or phase). As another example, the material may be a colloid in which one material of microscopically dispersed insoluble particles is suspended throughout another material. As another example, the material may be a gas bubble in which one material of microscopically dispersed gas bubbles is suspended throughout another material. As another example, the material may be an emulsion mixing two or more liquids that are normally immiscible (unmixable or unblendable).

In some embodiments, the material to be examined may be production fluid. For example, the material may be a mixture of oil, gas, and water in fluid from an oil well and/or a reservoir. In such embodiments, examination of the material may include an evaluation of the water fraction of the production fluid, indicating the water proportion and the hydrocarbon proportion of the fluid. Likewise, in such embodiments, examination of the material may include an evaluation of the gas-to-oil ratio of the production fluid, describing how many standard cubic feet of gas can be obtained for every stock tank barrel of oil. In some embodiments, the material to be examined may be a mixture of oil, sand, water, and/or clay in solid and/or fluid states from an oil well, a reservoir, and/or an oil-sand production facility. In such embodiments, examination of the material may include an evaluation of the water fraction of the production fluid, indicating the water proportion. Likewise, in such embodiments, examination of the material may include an evaluation of the ratios of oil, sand, and/or clay in the production fluid.

FIG. 1 illustrates an exemplary dielectric contrast analysis structure 100. The dielectric contrast analysis structure 100 includes a bulk dielectric substance 110. As illustrated, the bulk dielectric substance 110 is generally cylindrical, but a variety of shapes (e.g., rectangular solid, conical) may be applicable to various manufacturing or operational conditions. The bulk dielectric substance 110 is made of dielectric materials (e.g. plastics such as polyethylene, polycarbonate, or ceramics such as alumina, titania (titanium oxide), and ceramic ferrite). In many embodiments, the dielectric contrast analysis structure 100 will have two ends 130 (e.g., cylinder ends). The ends 130 may or may not have the same surface area. Receptacles 120 are formed in the bulk dielectric substance 110. Generally, the receptacles 120 will extend between the two ends 130. In some embodiments, the receptacles 120 may be formed during manufacture of the bulk dielectric substance 110 (e.g., cast molded). In some embodiments, the dielectric contrast analysis structure 100 and the receptacles 120 may be formed with additive manufacturing or 3D printing processes including but not limited to selective laser melting, selective laser sintering, fused deposition modeling, and stereolithography. In some embodiments, the receptacles 120 may be subsequently cut, bored, milled, or otherwise formed into the bulk dielectric substance 110 by removing material therefrom. A variety of techniques for creating receptacles 120 in a bulk dielectric substance 110 may be applicable to various manufacturing or operational conditions. The receptacles 120 are intended to receive, transport, transmit, and/or contain the material to be examined. In some embodiments, at least some of the receptacles 120 may have an opening in each end 130 of the dielectric contrast analysis structure 100. In the illustrated embodiment, the receptacles 120 are regular cylindrical shapes, disposed parallel with one another, extending between ends 130, and arranged in a symmetric array (e.g., parallel rows, parallel columns, rows perpendicular to columns). Other shapes (e.g., hexagonal, square), alignments, and/or arrangements (e.g., honeycomb) of receptacles 120 may be applicable to various manufacturing or operational conditions. In addition, the arrangements of receptacles 120 may contain defects and/or imperfections that may be used to localize the EM energy, and/or correlate the measured transmission with a specific point in the structure.

The configuration of the dielectric contrast analysis structure 100 may be selected based on the expected properties of the material to be examined. For example, the dielectric constant ($\kappa$, also referred to as the relative dielectric permittivity, $\varepsilon_r$) of the material of the bulk dielectric substance 110 may be selected to provide high contrast with the expected dielectric constant of the material to be examined. In some embodiments, the dielectric constant of the bulk dielectric substance 110 may be selected to be between about 1.0 and about 100, or between about 1.5 and about 3.5, or between about 2 and about 3, or approximately 2.3. In some embodiments, the expected dielectric constant of the material to be examined may be between that of air (about 1) to that of water (about 80+20i in the microwave domain, where i is the imaginary square root of −1.). As another example, the size, spatial distribution, and/or spatial density of the receptacles 120 in the bulk dielectric substance 110 may be selected to provide distinctive signals in the resultant electromagnetic radiation (discussed below). In some embodiments, the receptacles 120 may have a diameter of between about 1 mm and about 10 cm, or between about 10 mm and about 2 cm, or between about 100 mm and about 1.75 cm, or approximately 1.5 cm. In some embodiments, the spacing between adjacent receptacles 120, as measured from center to center, may be between about 0.1 cm and about 10.0 cm, or between about 1 cm and about 3 cm, or approximately 2 cm. Likewise, the size of the bulk dielectric substance 110 and/or number of receptacles 120 may be selected to provide distinctive signals in the resultant electromagnetic radiation. In some embodiments, the bulk dielectric substance 110 may have a diameter of between about 2 cm and about 100 cm, or 10 cm and about 30 cm, or between about 15 cm and about 25 cm, or approximately 21 cm. In some embodiments, the number of receptacles 120 in bulk dielectric substance 110 may be between about 10 and about 400, or between about 50 and about 100, or approximately 76.

As would be understood by one of ordinary skill in the art with the benefit of this disclosure, if the material to be examined in the receptacles has a non-zero conductivity $\sigma$, the full dielectric constant may be written as a complex number of the form $\varepsilon=\varepsilon_r+I\ \sigma/\omega$, where $\varepsilon_r$ may itself be a complex number as defined above and $\omega$ is the frequency. Conductivity of brine in typical hydrocarbon management environments can range anywhere from 1 mS/m to 10 S/m. It is convenient to define an index of refraction $n=\sqrt{(\varepsilon\mu)}$, where $\mu$ refers to the magnetic permeability. In almost all cases of relevance to this disclosure, $\mu=1$, and the index of refraction can be simply written as the $n=\sqrt{\varepsilon}$. Since the dielectric constant may be a complex number, the index of refraction may also be a complex number with a real and imaginary part. Alternatively, it is also common to define an impedance $Z=\sqrt{(\mu/\varepsilon)}$. Depending on the context, this disclosure covers a measurement of any function of the dielectric constant of the examined medium, which can be determined, once the dielectric constant is obtained.

As will be further discussed below, the dielectric contrast analysis structure 100 is configured to receive incident electromagnetic radiation and transmit resultant electromagnetic radiation, while the receptacles 120 are configured to contain and/or channel the flow of material to be examined. Therefore, the height (i.e., the distance between ends 130) of the dielectric contrast analysis structure 100 may be selected to better receive and transmit the electromagnetic radiation.

In some embodiments, the height of dielectric contrast analysis structure 100 may be between about 2 cm and about 50 cm, or between about 10 cm and about 20 cm, or approximately 15 cm. In some embodiments, the dimensions of dielectric contrast analysis structure 100 may be configured to dispose the dielectric contrast analysis structure 100 within a wellbore, tubular within a wellbore, wellhead, surface pipeline, subterranean pipeline, ocean bottom pipeline, riser, or other equipment for handling production fluid.

Figure 2:
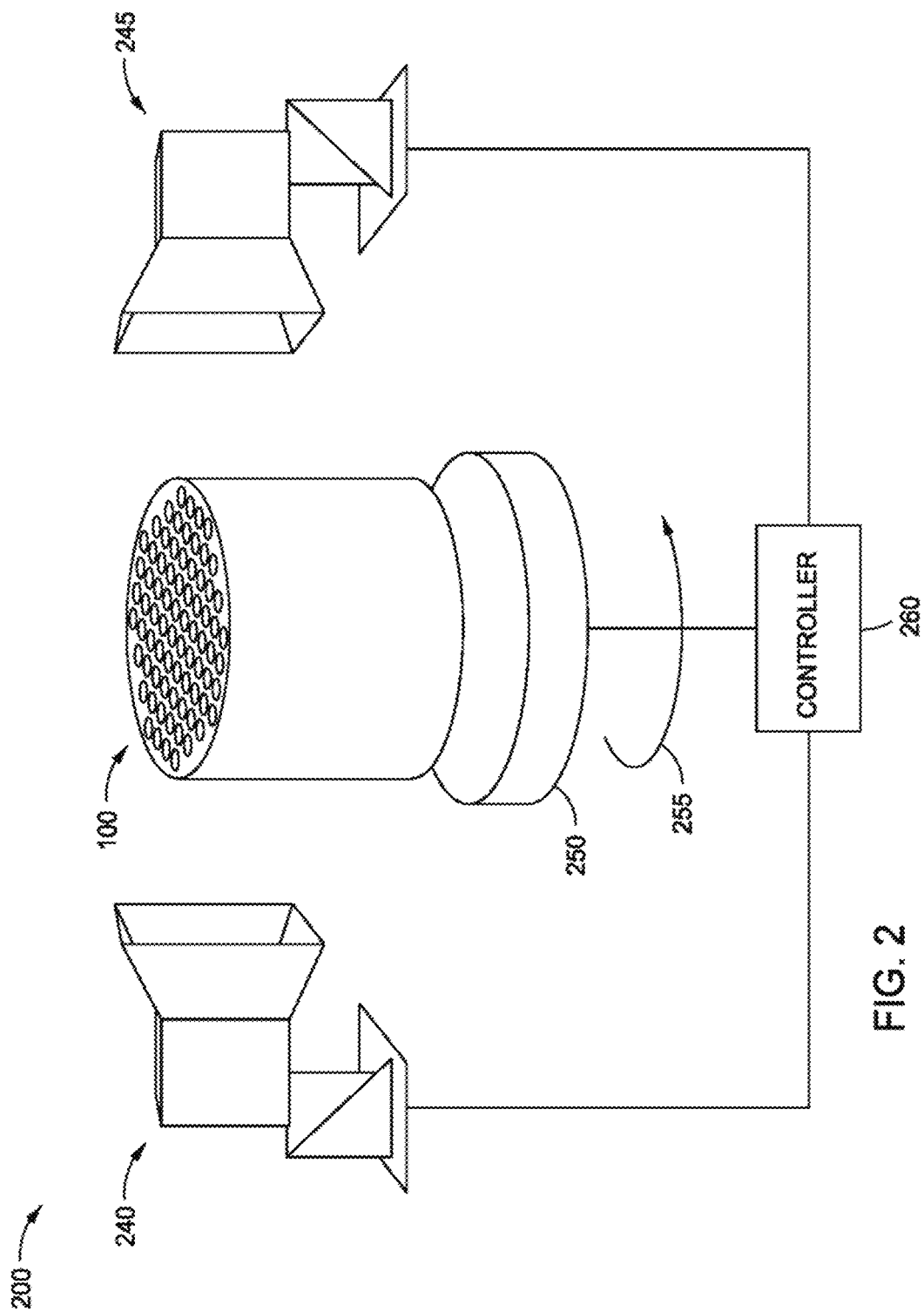
FIG. 2 illustrates an analysis system, including the dielectric contrast analysis structure of FIG. 1, according to embodiments disclosed herein.
Figure 4A:
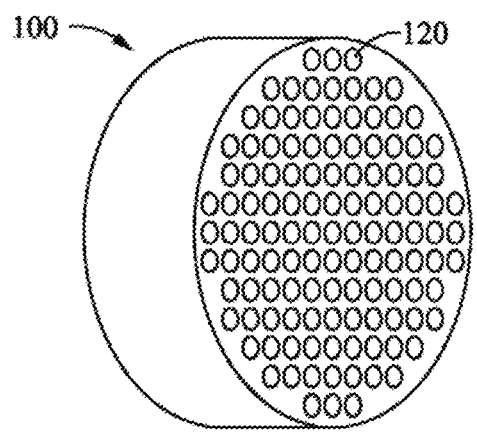
FIGS. 4A-4F illustrate examples of different amounts and types of material to be examined in receptacles of the dielectric contrast analysis structure of FIG. 1.
Figure 4B:
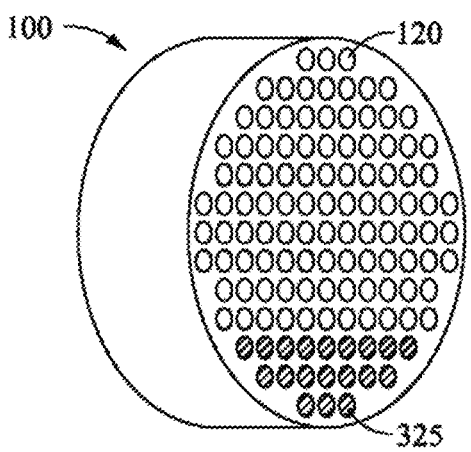
Figure 4C:
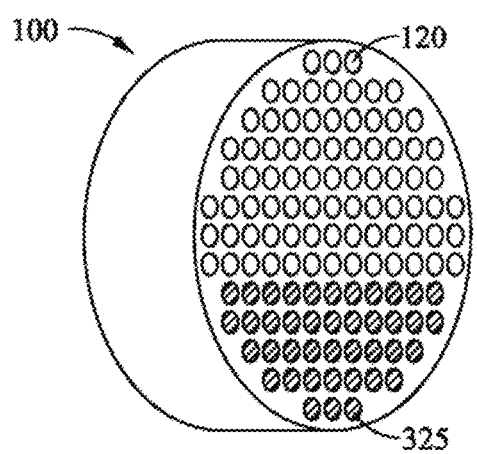
Figure 4D:
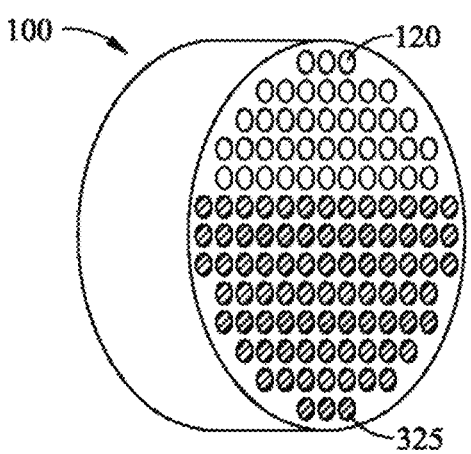
Figure 4E:
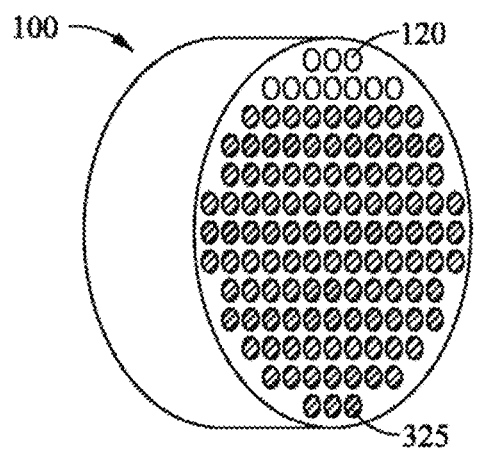
Figure 4F:
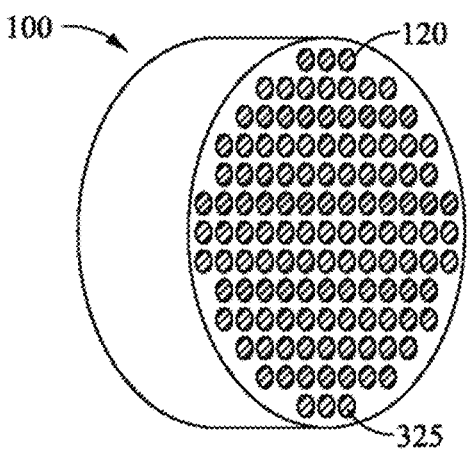

FIG. 2 illustrates an exemplary analysis system 200. Analysis system 200, according to embodiments disclosed herein, generally includes a dielectric contrast analysis structure 100, an electromagnetic radiation source, such as transmitting antenna 240, and an electromagnetic radiation detector, such as receiving antenna 245. Other non-limiting examples of electromagnetic radiation source include a device to generate a time varying electromagnetic field (for example a coil, a translating/rotating/oscillating permanent magnet such as Neodymium magnet, a electromagnet, a dipole antenna, a Yagi-Uta antenna, and a waveguide). Other non-limiting examples of an electromagnetic radiation detector include a device to receive the electromagnetic radiation from at least one point or averaged over a sensing area, and/or to convert the electromagnetic radiation signal to a digital or analogue signal that can be interpreted by a computer or observer, such as pickup coils, a dipole antenna, a Yagi-Uta antenna, or superconducting RF SQUID detector. The transmitting/receiving antennas 240/245 may be, for example, radio frequency and/or microwave antennas, such as 3115 Double-Ridged Guide Antenna available from ETS-Lindgren. As illustrated, the transmitting antenna 240 and receiving antenna 245 are generally on opposite sides of dielectric contrast analysis structure 100. Transmitting antenna 240 is configured to expose the dielectric contrast analysis structure 100 to incident electromagnetic radiation. An electromagnetic radiation source, such as the transmitting antenna 240 may be configured to generate incident electromagnetic radiation having one or more frequencies between about 1 MHz and about 100 GHz, or between about 100 MHz and about 50 GHz, or between about 1 GHz and about 20 GHz, or approximately 10 GHz. In some embodiments, the incident electromagnetic radiation may include a frequency band of interest that is based on the length scales and/or dielectric properties of the dielectric contrast analysis structure 100. In some embodiments, the incident electromagnetic radiation may be linearly polarized (e.g., transverse electric modes). An electromagnetic radiation detector, such as the receiving antenna 245 is configured to detect resultant electromagnetic radiation from the exposed dielectric contrast analysis structure 100. Receiving antenna 245 may include one or more electromagnetic radiation detectors, which may be distributed in a row, as illustrated in FIG. 3, or around the perimeter of dielectric contrast analysis structure 100, or in other configurations as applicable to various manufacturing or operational conditions. The receiving antenna is not limited to sensing electromagnetic radiation with the same polarization as the source.

As would be understood by one of ordinary skill in the art with the benefit of this disclosure, radiation from transmitting antenna 240 incident on dielectric contrast analysis structure 100 may be absorbed, deflected, reflected, refracted, scattered, phase-shifted, frequency-multiplied, and/or otherwise affected by interactions at interfaces of dielectric discontinuity (e.g., the exterior surface of dielectric contrast analysis structure 100, perimeters of each receptacle 120). Consequently, the path taken by radiation from transmitting antenna 240 may be bent or changed when traveling through dielectric contrast analysis structure 100. In order to detect resultant electromagnetic radiation from the exposed dielectric contrast analysis structure 100, the receiving antenna 245 may be configured to receive resultant radiation at a variety of angles around dielectric contrast analysis structure 100 in addition to, or in lieu of, directly opposite from transmitting antenna 240.

FIG. 3 illustrates an exemplary convention for referencing the angle at which resultant electromagnetic radiation exits the dielectric contrast analysis structure 100. Deflection angle θ is formed between the path of the incident electromagnetic radiation from the transmitting antenna 240 and the path of the resultant electromagnetic radiation exiting from the dielectric contrast analysis structure 100. Deflection angle θ is deemed to be 0° when the resultant radiation exits along the same path as the incident radiation. Consequently, radiation that is reflected at the incident surface of the dielectric contrast analysis structure 100 would be deemed to have a deflection angle of 180°.

In some embodiments, analysis system 200 also includes a rotation actuator, such as stage 250, as illustrated in FIG. 2. When placed on or coupled to stage 250, dielectric contrast analysis structure 100 may be caused to rotate 255 relative to transmitting antenna 240 and receiving antenna 245. An exemplary stage 250 suitable for this purpose includes X-RST120AK Motorized rotary stage available from Zaber Technologies. Other rotation actuators (non-limiting examples include motorized rotation stage with stepper motor, annular rotation stage, manual rotation stage, and a spinner wheel at an end 130) may be considered to cause dielectric contrast analysis structure 100 to rotate 255 (relative to the transmitting/receiving antennas 240/245), as applicable to various manufacturing or operational conditions. Likewise, other configurations of the components may be considered. For example, the rotation actuator could be an annular stage, with dielectric contrast analysis structure 100 in the annulus. Transmitting antenna 240 and receiving antenna 245 could be disposed on the annular stage. Rotation of the annular stage would cause relative rotation 255 between the dielectric contrast analysis structure 100 and the transmitting/receiving antennas 240/245. Similar results may be achieved without relative rotation 255, such as disposing multiple transmitting antennas 240 and/or receiving antennas 245 around the perimeter of dielectric contrast analysis structure 100.

Analysis system 200 may also include a controller 260. Controller 260 may be in communication with transmitting antenna 240, receiving antenna 245, and/or stage 250. Controller 260 may send control signals. For example, controller 260 may send control signals to transmitting antenna 240 to initiate transmission of electromagnetic radiation. The control signals may specify, for example, the timing of the radiation exposure, the power and/or frequency of the electromagnetic radiation, and/or the direction of the electromagnetic radiation as it leaves transmitting antenna 240 (e.g., beamforming). Controller 260 may send control signals to stage 250, for example to control timing, rotation direction, and/or speed of the rotation 255 of the dielectric contrast analysis structure 100 (relative to the transmitting/receiving antennas 240/245). Controller 260 may also receive feedback and/or readout data signals. For example, controller 260 may receive data signals from receiving antenna 245 indicative of the detected electromagnetic radiation. Controller 260 may process the feedback and/or data signals. Controller 260 may generate new control signals based, at least in part, on the received and/or processed feedback and/or data signals. Controller 260 may be a single device (e.g., network analyzer) or a collection of separate, but communicatively coupled, devices (e.g., a computer network). For example, controller 260 may include a network analyzer, such as N5230A PNA-L Network Analyzer available from Keysight Technologies. Similarly, in other examples, controller 260 may include a desktop computer, a spectral analyzer, a RF/Microwave signal generator, and/or an amplifier.

Although FIG. 2 seems to illustrate the ends 130 being disposed on the upper and lower (with respect to gravity) sides of dielectric contrast analysis structure 100, it should be understood that many operational configurations will include other orientations of the analysis system 200. In some embodiments, for example, the axis of rotation of dielectric contrast analysis structure 100 may be perpendicular to the gravitational force. In such embodiments, and when the receptacles 120 are open at ends 130, heavier substances may flow through the lower (with respect to gravity) receptacles 120, while lighter substances (such as air with respect to oil) may flow through the higher receptacles 120.

During operation, some or all of the receptacles 120 may contain material to be examined. For example, FIGS. 4A-4F illustrate six different numbers of receptacles 120 containing material to be examined 325. It is anticipated that some operational usages of dielectric contrast analysis structure 100 will utilize gravity to direct which receptacles 120 first fill with material to be examined 325.

Figure 5:
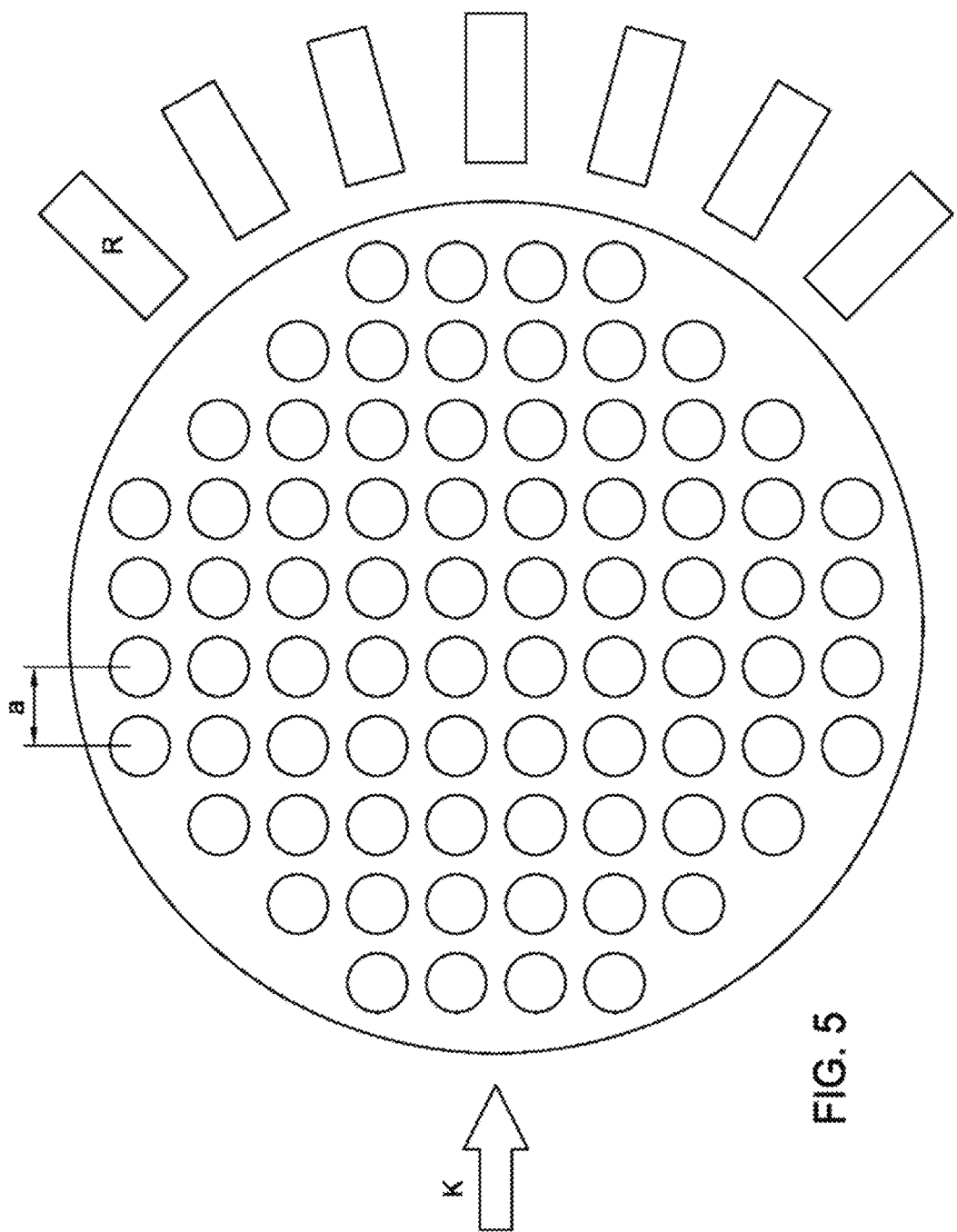
FIG. 5 illustrates a convention for referencing the results of incident electromagnetic radiation with a periodic dielectric contrast analysis structure, according to embodiments disclosed herein.

It is currently believed that after exposing the dielectric contrast analysis structure 100 with periodicity a to an incident electromagnetic radiation k, the resultant electromagnetic radiation R as measured by one or more electromagnetic radiation detectors (e.g. around the perimeter of dielectric contrast analysis structure 100 as illustrated in FIG. 5), can be described according to Bloch's theorem:

$$H_k(r) = e^{ikr} u_k(r) \tag{1}$$

$$u_k(r) = u_k(r+a) \tag{2}$$

where:

$$\left\{ \nabla \times \frac{1}{\varepsilon(r)} \nabla \times \right\} H(r) = \frac{\omega^2}{c^2} H(r) \tag{3}$$

$$\varepsilon(r) = \varepsilon(r+a) \tag{4}$$

Note that the magnetic field H has been expanded as a plane-wave in Equation 1. The symmetry of the lattice has been exploited in Equation 2. Note that Equation 3 is Maxwell's wave equation in frequency (w) space, where c is the permittivity (or dielectric constant) of the dielectric contrast analysis structure with the material to be examined, normalized to the permittivity of free space $\varepsilon_0 = 8.85 \times 10^{-12}$ F/m, and c is the speed of light. Equation 4 is thought to be valid when the material to be examined homogeneously fills all the receptacles.

The resultant electromagnetic radiation R may thus have frequency and/or angle dependency when exposed to incident electromagnetic radiation of wavelengths comparable to periodic feature sizing, for example when the ratio of wavelength and feature size is between about 0.01 and about 100, or between about 0.1 and about 10, or between about 0.4 and about 2.5.

Figure 6:
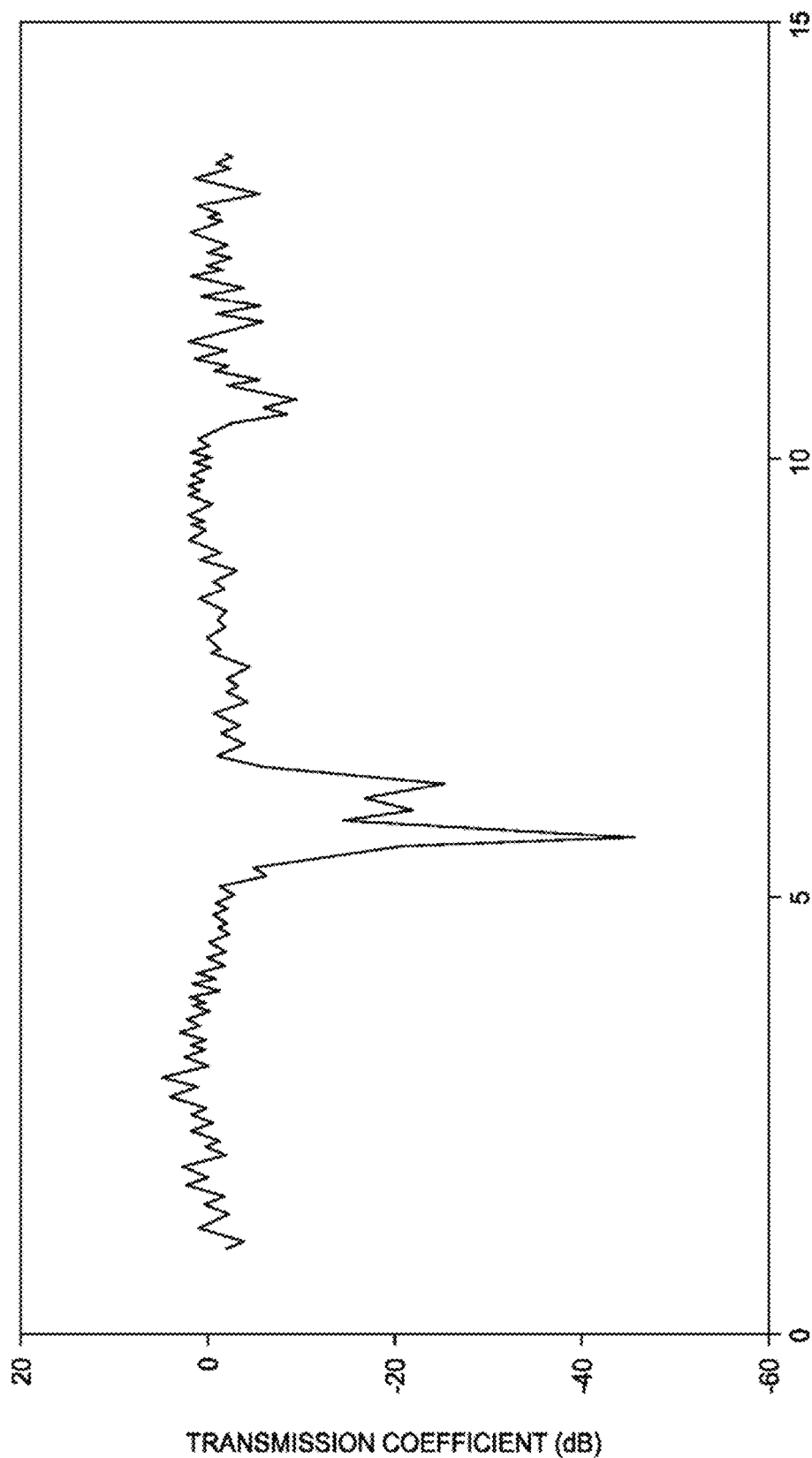
FIG. 6 illustrates measurement of transmission coefficients as a function of frequency of the incident electromagnetic radiation at a single angle/configuration for the dielectric contrast analysis structure of FIG. 4A.

When the dielectric contrast analysis structure 100 contains air (dielectric constant of about 1.0) in the receptacles 120, an anisotropic interaction may be observed between the incident electromagnetic radiation and the dielectric contrast analysis structure 100. The observed response may be related to a photonic band structure. A network analyzer (e.g., of controller 260) may be used to initiate transmission of electromagnetic radiation in the microwave band (about 1 GHz to about 13.5 GHz) from the transmitting antenna 240, for example at about 1 mW power. The receiving antenna 245 may be used to measure the resultant electromagnetic radiation from the dielectric contrast analysis structure 100. FIG. 6 illustrates a typical transmission coefficient (in dB, defined as power ratio in decibels) measurement as a function of frequency of the incident electromagnetic radiation at a single angle/configuration (e.g., the receiving antenna 245 directly opposite from the transmitting antenna 240) for the air-containing dielectric contrast analysis structure 100 of FIG. 4A. The transmission coefficient of FIG. 6 represents a ratio of energies between resultant electromagnetic radiation and incident electromagnetic radiation, normalized by data acquired with a control structure which does not have any receptacles 120, while having the same diameter, height and dielectric constant of the dielectric contrast analysis structure 100.

Figures 7A, 7B:
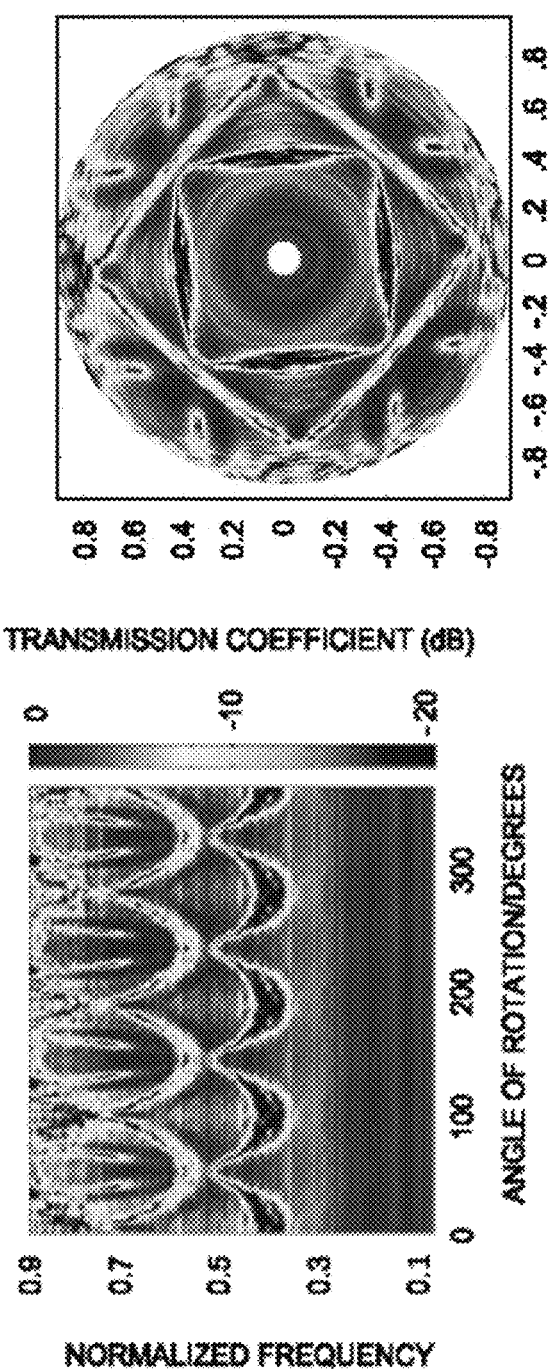
FIG. 7A illustrates an intensity plot of the transmission coefficients from the dielectric contrast analysis structure of FIG. 4A as a function of orientation/angle.
FIG. 7B illustrates a polar intensity plot of the transmission coefficients from the dielectric contrast analysis structure of FIG. 4A as a function of orientation/angle.

Analysis system 200 may be used to obtain measurements of transmission coefficients by rotating the dielectric contrast analysis structure 100, for example with stage 250. Similar to the results of FIG. 6, the receptacles 120 of dielectric contrast analysis structure 100 contain air (e.g., FIG. 4A). The corresponding results can be represented as an intensity plot, as shown in FIG. 7A. Here, the X-axis is the orientation or rotational angles, and the Y-axis is the normalized frequency. The normalized frequency is the actual frequency divided by the characteristic frequency for the dielectric contrast analysis structure 100 with periodicity a of 2 cm (about 15 GHz in this case). The color variations in the intensity plot represents the transmission coefficient at the various frequencies and/or orientations. In general, red indicates higher transmission coefficients, and blue represents lower transmission coefficients. The same data may be represented as a polar intensity plot, as shown in FIG. 7B. Here, the angular axis is the orientation or rotational angle, and the radial axis is the normalized frequency. Both FIG. 7A and FIG. 7B show a 4-fold symmetry that is thought to be a result of the symmetry of the square array of receptacles 120. The dark blue zones with very small transmission coefficients, conventionally called a photonic bandgap, reflects the fact that for a specific direction of propagation some frequency bands or modes of electromagnetic radiation cannot generally be transmitted across the photonic crystal due to the high dielectric contrast between the bulk dielectric substance 110 and the air-filled receptacles 120. As this physical phenomena is scale invariant over a broad band of frequencies, it is currently believed that the size, spatial distribution, and/or spatial density of the receptacles 120 in the bulk dielectric substance 110 may be selected so that the dielectric contrast analysis structure 100 has a characteristic frequency from 1 MHz to 100 GHz.

In another operational configuration, the material to be examined 325 in the receptacles 120 includes air, oil, water, and/or mixtures thereof. For example, analysis system 200 may be used to perform a series of experiments to understand the effects of filling a fraction of the receptacles 120 with water. FIGS. 8A-8F illustrate dielectric contrast analysis structure 100 having different fractions of the total number of receptacles 120 filled with water 325. For the examples shown from FIG. 8 to FIG. 13, the bulk dielectric substance 110 is made of polycarbonate. The dielectric contrast analysis structure 100 has a diameter of about 89 mm and a height of about 50 mm. The receptacles 120 have a diameter of about 5.0 mm, with the centers of adjacent receptacles 120 having about 6.67 mm separation. The transmitting/receiving antennas 240/245 may be double ridge horn antennas, such as 3116C Double-Ridged Waveguide Horn available from available from ETS-Lindgren. The controller 260 may include a network analyzer, such as N5244A PNA-X Network Analyzer available from Keysight Technologies. Stage 250 may include X-RSW60A Motorized rotary stage available from Zaber Technologies. FIGS. 9A-9F illustrate polar intensity plots of the results from the experimental set-ups illustrated in FIGS. 8A-8F, respectively. Instead of the 4-fold symmetry in the polar intensity plot for a fully air-filled structure (FIG. 9A), the intensity plot for low fractions of water (FIGS. 9B and 9C) start to experience a 2-fold symmetry as this water-filled stratified (or density separated) morphology breaks the 4-fold symmetry from the dielectric structure. Data images at higher fractions of water (FIGS. 9D and 9E) show larger ring-shaped structure with low transmission coefficient. It is currently believed that stratified morphology or substance distribution can be identified by observing a 2-fold symmetry, and the existence of attenuating substance such as water can be identified by observing large areas of low transmission coefficient in the intensity plots and/or the polar intensity plots.

As another example, analysis system 200 may be used to perform a series of experiments to understand the effects of filling a fraction of the receptacles 120 with oil. FIGS. 10A-10F illustrate dielectric contrast analysis structure 100 having different fractions of the total number of receptacles 120 filled with oil (as the material to be examined 325). The oil may be silicone oil, with viscosity such as 100 cSt. FIGS. 11A-11F illustrate polar intensity plots of the results from the experimental set-ups illustrated in FIGS. 10A-10F, respectively. Instead of the 4-fold symmetry in the polar intensity plot for a fully air-filled structure (FIG. 11A), the intensity plot for low fractions of oil (FIGS. 11B and 11C) start to experience a 2-fold symmetry as this oil-filled stratified morphology breaks the 4-fold symmetry from the dielectric structure. Data images at higher fractions of oil (FIGS. 11D and 11E) show larger isotropic area with high transmission coefficient. It is currently believed that stratified morphology or substance distribution can be identified by observing a 2-fold symmetry.

As another example, analysis system 200 may be used to perform a series of experiments to understand the effects of filling a first fraction of the total number of receptacles 120 with water 325-*w* and a second fraction of the receptacles 120 with oil 325-*o*. FIGS. 12A-12F illustrate dielectric contrast analysis structure 100 having different fractions of water/oil-filled receptacles 120. In this example, the water 325-*w* and the oil 325-*o* are naturally separated by density (assuming gravity is pointing down), the water 325-*w* being below the oil 325-*o*. FIGS. 13A-13F illustrate polar intensity plots of the results from the experimental set-ups illustrated in FIGS. 12A-12F, respectively.

Figure 14:
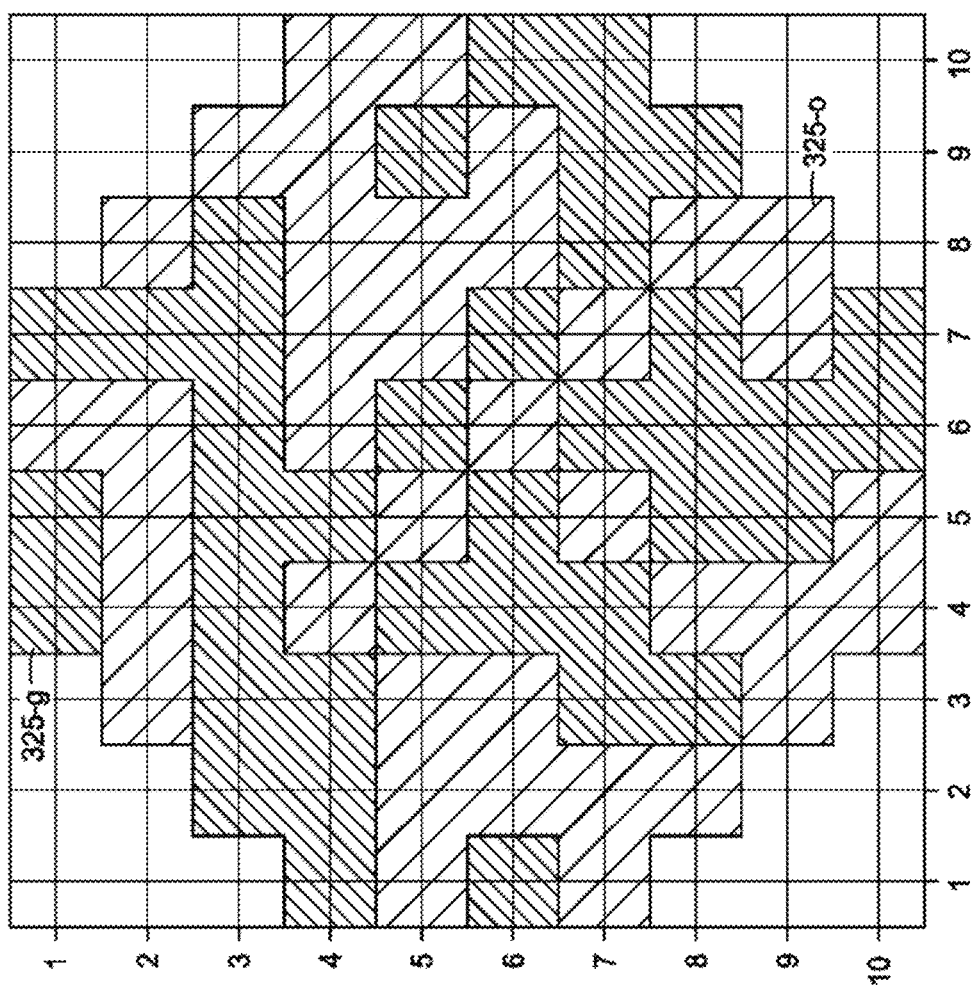
FIG. 14 illustrates an exemplary configuration of different amounts and types of material to be examined in receptacles of the dielectric contrast analysis structure of FIG. 1.
Figure 15E:
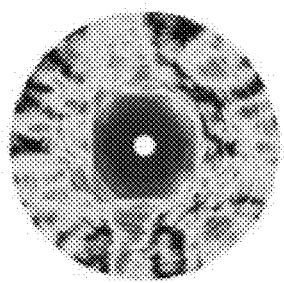
FIGS. 15A-15J illustrate polar intensity plots of the transmission coefficients from the dielectric contrast analysis structure exemplified by FIG. 14 with increasing fractions of oil.
Figure 15D:
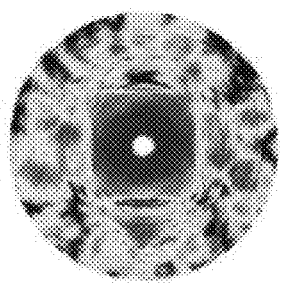
Figure 15C:
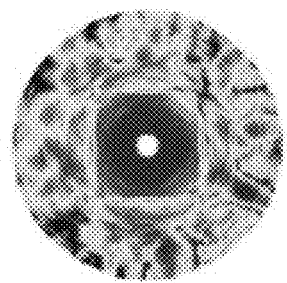
Figure 15B:
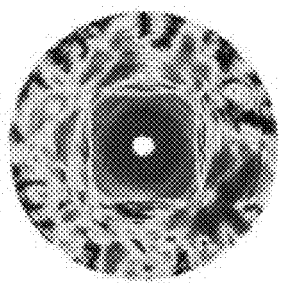
Figure 15A:
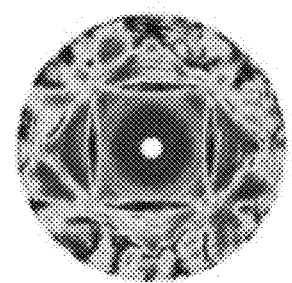
Figure 15J:
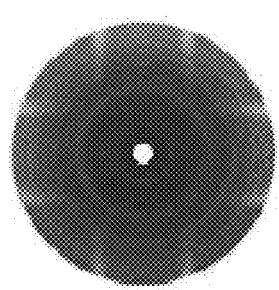
Figure 15I:
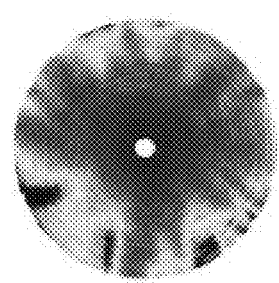
Figure 15H:
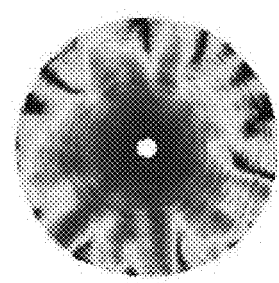
Figure 15G:
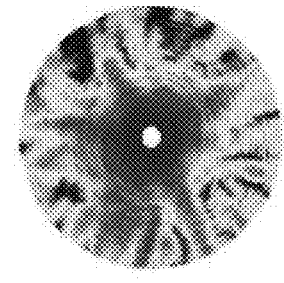
Figure 15F:
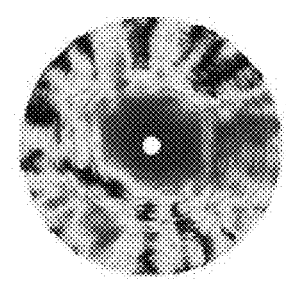

As another example, analysis system 200 may be used to perform a series of experiments to understand the effects of filling a first fraction of the total number of receptacles 120 with gas 325-*g* and a second fraction of the receptacles 120 with oil 325-*o*, wherein the distribution of the first and second fractions of receptacles 120 is random (or at least not separated by density). These experiments may indicate the behavior of analysis system 200 with multiphasic fluids. For the examples shown from FIG. 14 to FIG. 15, the bulk dielectric substance 110 is made of polyethylene. The dielectric contrast analysis structure 100 has a diameter of about 21 cm and a height of about 15 cm. The receptacles 120 have a diameter of about 1.5 cm, with the centers of adjacent receptacles 120 having about 2.0 cm separation. The transmitting/receiving antennas 240/245 may be double ridge horn antennas, such as 3115 Double-Ridged Waveguide Horn available from available from ETS-Lindgren. The controller 260 may include a network analyzer, such as N5230 PNA-L Network Analyzer. Stage 250 may include X-RST120AK Motorized rotary stage available from Zaber Technologies. FIG. 14 illustrates an example of dielectric contrast analysis structure 100 having some receptacles 120 filled with gas 325-g and other receptacles 120 filled with oil 325-o with a fraction of oil at 50%. In this example, the oil may be polyalphaolefin viscosity grade 4 ("PAO4"). FIGS. 15A-15J illustrate representative polar intensity plots of the results from experimental set-ups with increasing fractions of oil (10%, 20%, 30%, 40%, 50%, 60%, 70%, 80%, 90%, and 100%, respectively). The experimental procedures to obtain the polar intensity plots of FIGS. 15A-15J may include repeating measurements several times for each fraction-of-oil configuration. The experimental procedures may also include changing the particular distribution of oil-filled receptacles 120 between each measurement. It is currently believed that the isotropic high transmission image data at 100% (FIG. 15J) is due to a very low dielectric contrast between the polyethylene structure ($\varepsilon_r \sim 2.3$) and the PAO4 oil-filled holes ($\varepsilon_r \sim 2.1$).

Figure 16:
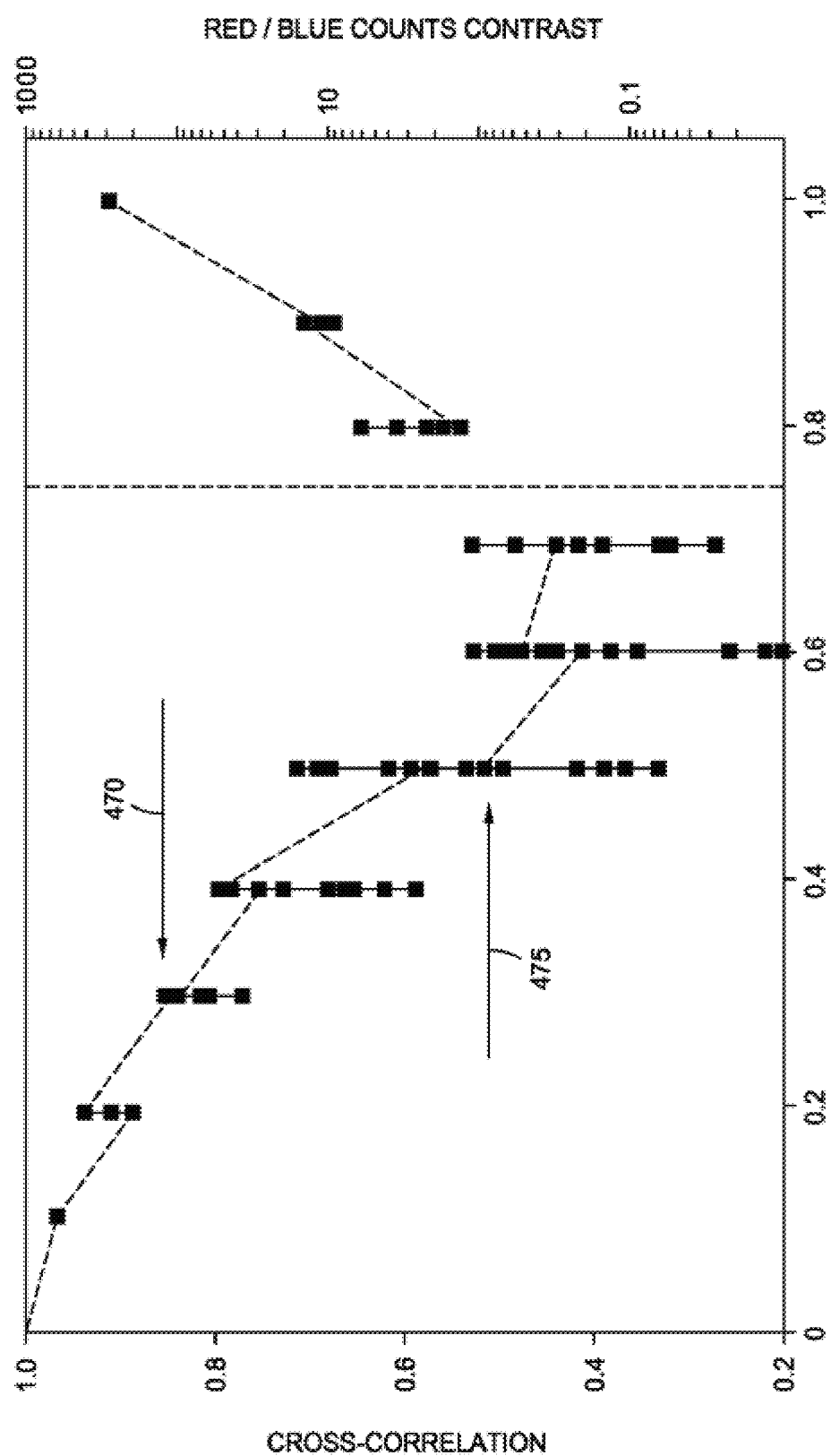
FIG. 16 illustrates a statistical analysis of one hundred polar intensity plots across different fractions of oil exemplified by FIGS. 15A-15J.

In some embodiments, analysis system 200 may be utilized to estimate oil fraction of the material to be examined 325. For example, FIG. 16 illustrates a statistical analysis of the polar intensity plots from one hundred sets of experiments across different fractions of oil from 0% to 100% exemplified by FIGS. 15A-15J, as measured as a function of Fraction of Oil (X-axis). Note that, at higher oil fractions, for example from 80% to 100% (data similar to and exemplified by FIGS. 15H-15J), the area with higher transmission grows consistently without particular symmetry. This effect can be characterized by a red-to-blue-counts ratio $$\left(\frac{\text{number of red pixels}}{\text{number of blue pixels}}\right)$$

as plotted on the right side of the vertical black dashed line in FIG. 16. Here, the number of red pixels is counted when the transmission coefficients are between about 0 to about −2 dB, and the number of blue pixels is counted when the transmission coefficients are below about −10 dB in the frequency band (e.g., normalized frequency) between about 0.32 and about 0.48. For data images of the same oil fraction, the resulting ratio of red/blue counts yields the vertical range in FIG. 16. From 80% to 100% (data similar to and exemplified by FIGS. 15H-15J), the observed ranges do not overlap, indicating the capability of the method to predict the fraction of oil in the dielectric contrast analysis structure 100 with less than 10% uncertainty.

At lower oil fraction, for example from 10% to 50% (FIGS. 15A-15E), the inner square-shaped blue zone is fading towards higher transmission coefficient and brighter color. This may be characterized by cross-correlating the relevant part of a specific data image (normalized frequency between about 0.32 and about 0.4) to the same part of 0% data image (FIG. 7B). The whole set of cross-correlation results are shown to the left side of the vertical black dashed line in FIG. 16. For all data images of the same oil fraction, the resulting cross-correlations may show up as a vertical range in FIG. 16. From 10% to 20% (data similar to and exemplified by FIGS. 15A-15B), these vertical ranges do not overlap, indicating the capability of the method to predict the fraction of oil in the dielectric structure with less than 10% uncertainty. From 30% to 70% (data similar to and exemplified by FIGS. 15C-15G), however, the vertical ranges do overlap, and the method is capable of predicting the fraction of oil with about 10% uncertainty in these scenarios. For example, the cross-correlations of the tests 470 at lower oil phase fractions indicate that these set-ups contain about 30%±0% fraction of oil, and the cross-correlations of the tests 475 at higher oil phase fractions indicate that these set-ups contain 60±10% fraction of oil. The test results are consistent with actual fraction of oil used (about 30% for tests 470, and about 60% for tests 475).

Figure 17:
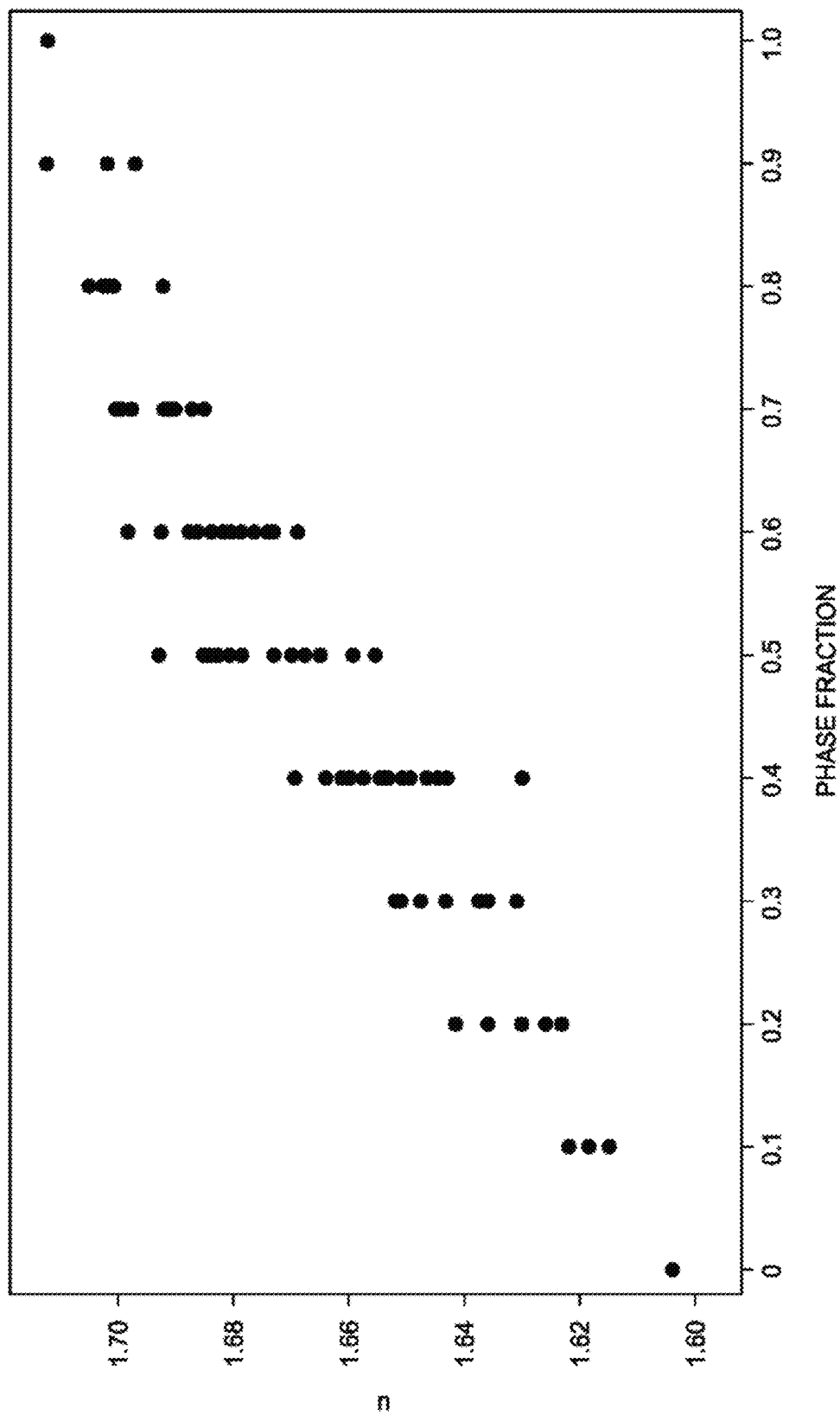
FIG. 17 illustrates a physics-based analysis of one hundred polar intensity plots across different fractions of oil exemplified by FIGS. 15A-15J.

As another example, FIG. 17 illustrates a physics-based analysis of the polar intensity plots from one hundred sets of experiments across different fractions of oil from 0% to 100% exemplified by FIGS. 15A-15J. In FIG. 17, by using effective media theory, the effective indices of refraction (n) may be extracted and plotted for only the long wavelength or low frequency part of the data (normalized frequency below about 0.15). Similar to the statistical method illustrated in FIG. 16, for all data of the same oil fraction, the resulting indices of refraction show up as a vertical range in FIG. 17. From the overlapping of those vertical ranges, this method may be capable of predicting the fraction of oil in the dielectric structure with about ±10% uncertainty. The uncertainty in the phase fraction inferred from the various techniques discussed to this point is greatest between 40 and 60% in the fraction of oil. This maximum in uncertainty near the middle of the phase fraction range has also been observed with commercially available tools for measuring phase fractions.

Figure 18B:
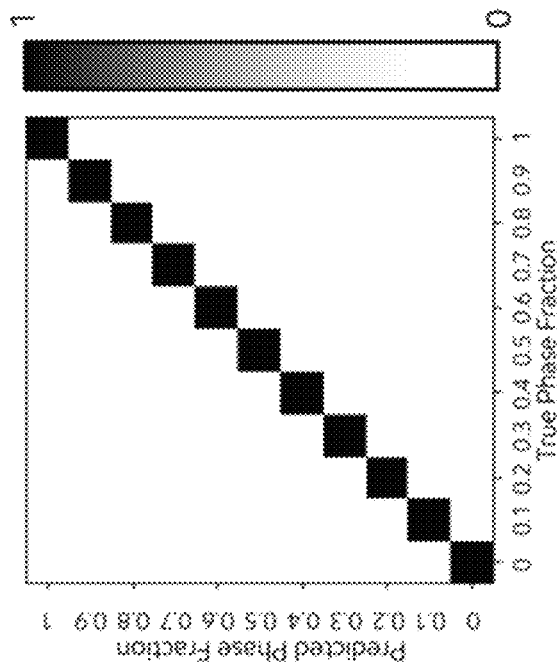
FIG. 18B illustrates the prediction accuracy with a 2D probability histogram by plotting the predicted phase fractions versus the true phase fractions through a machine-learning analysis of one hundred polar intensity plots across different fractions of oil exemplified by FIGS. 15A-15J.
Figure 18C:
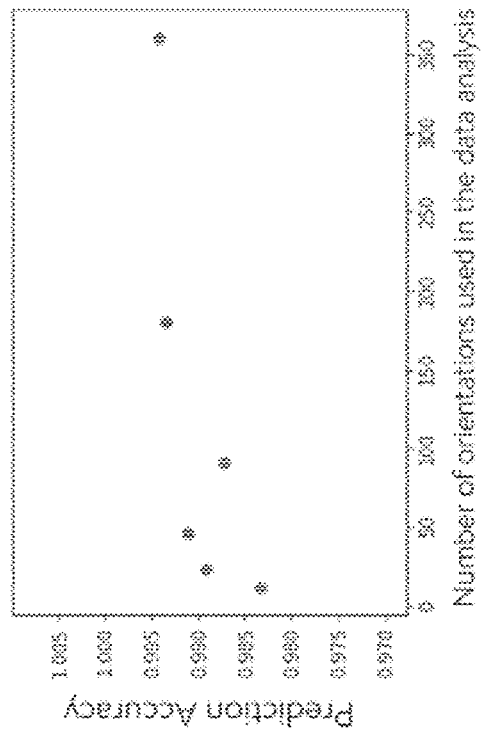
FIG. 18C illustrates the sensitivity study of prediction accuracy when a subset (10) of frequencies and orientations (from 12 to 360 as X-axis) are used in machine learning analysis.
Figure 18A:
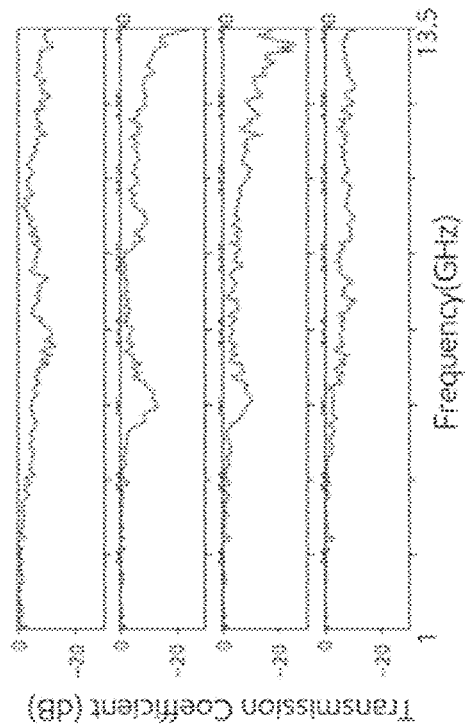
FIG. 18A illustrates four exemplified sets of training input data from experiments with different fractions of oil (20%, 30%, 40%, and 50% from top to bottom), and each of them includes one transmission coefficient spectrum from one measurement orientation.

As another example, FIG. 18 illustrates a machine-learning analysis of the polar intensity plots from one hundred sets of experiments across different fractions of oil from 0% to 100% exemplified by FIGS. 15A-15J. A machine-learning algorithm, may be used to classify the 360-degree data from 100 experiments using one or more machine learning methods including a Monte Carlo cross-validation method, k-Nearest Neighbor method, Support Vector Machine method, Random Forests method, and any Deep Learning methods such as Artificial Neural Network and Convolutional Neural Network. Dimensionality reduction may be performed first to reduce the number of degrees of freedom in the data. For example, a thresholding procedure may be used to assign transmission coefficients into one or more bins based on the dB loss. The data from 100 experiments are randomly split into one or more different sets of 80/20 non-overlapping training and test examples. One set of training input data could include transmission coefficient spectra/spectrum from one or more measurement orientations in an experimental polar intensity plot. For example, if one set of training input data include the complete data from an experimental polar intensity plot, there would be 80 sets of training input data from 80 randomly chosen experiments. As another example, if one set of training input data include a single transmission coefficient spectrum at a specific angle of an experimental polar intensity plot, there would be 28800 sets of training input data from 80 randomly chosen experiments each with 360 different angles. As a specific example, FIG. 18(a) shows four sets of training input data from experiments with different fractions of oil (20%, 30%, 40%, and 50% from top to bottom), and each of them includes one transmission coefficient spectrum from one measurement orientation. The training input data along with data labels (fractions of oil) are fed into one or more supervised Machine Learning classifiers to build a training model. The accuracy of the training model is then tested on the holdout test data. The procedure is repeated for all training/test examples, and the resulting classifier algorithm is the mean of the classifiers. The 2D probability histogram in FIG. 18(b) shows the prediction accuracy by plotting the predicted phase fractions versus the true phase fractions. The greyscale colorbar represents the probability of detection, with black represents 100% and white represents 0%. FIG. 18(b) utilizes data from all 360 orientations of measurements, all frequencies and all 100 experiments, and it shows an overall prediction accuracy of 99.5%. It is currently believed that even higher accuracy (or lower prediction error) can be obtained if we have a larger training data set.

It is currently believed that for some practical applications, less numbers of orientations and frequencies can be used in the data acquisition while providing sufficient prediction accuracy. For example, a sensitivity study on the method and system was conducted by testing the data analysis method with a subset of orientations and frequencies. During this process, we can choose a selection of orientations and frequencies to test prediction accuracy under certain system constraints in some applications. As an example, FIG. 18(c) shows the overall prediction accuracy when only use a subset (10) of frequencies and different numbers of orientations (from 12 to 360 as X-axis) in all data analysis including training machine learning models and data validation was used. As shown in FIG. 18(c), it is currently believed that more than 98% prediction accuracy can be achieved with no more than 12 orientations and no more than 10 different frequencies.

In all practical applications, the aforementioned plotting and/or analysis must be used in conjunction with a data analysis system (e.g., a laptop and/or a high-speed computer) programmed in accordance with the disclosures herein. In some embodiment, the data analysis system is a high performance computer ("HPC"), as known to those skilled in the art. Such high performance computers typically involve clusters of nodes, each node having multiple CPU's and computer memory that allow parallel computation. The models may be visualized and edited using any interactive visualization programs and associated hardware, such as monitors and projectors. The architecture of system may vary and may be composed of any number of suitable hardware structures capable of executing logical operations and displaying the output according to the present disclosure. Those of ordinary skill in the art are aware of suitable supercomputers available from Cray or IBM.

Figure 19:
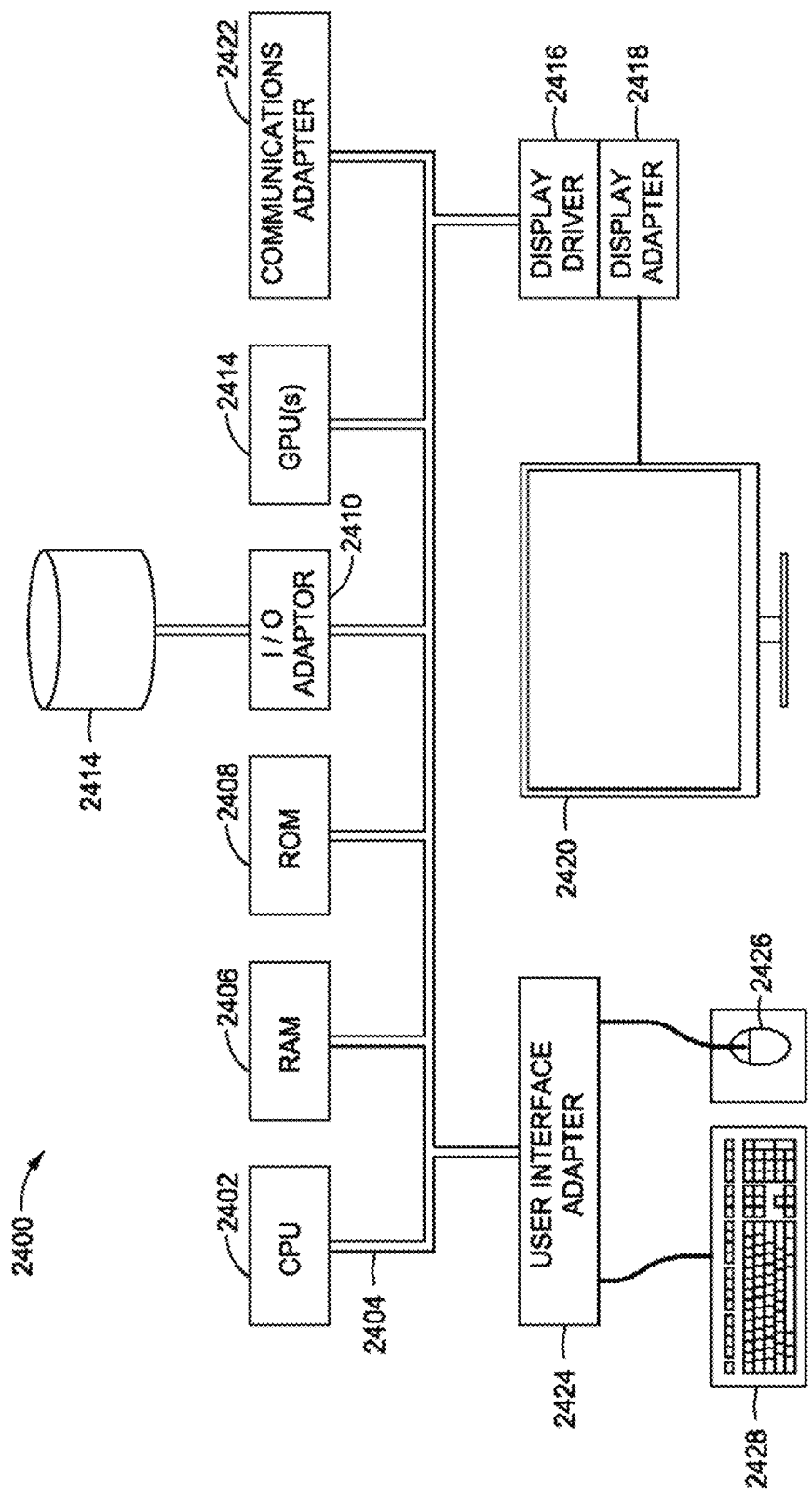
FIG. 19 illustrates a block diagram of a data analysis system upon which the plotting and/or analysis disclosed herein may be embodied.

FIG. 19 illustrates a block diagram of a data analysis system 2400 upon which the aforementioned plotting and/or analysis may be embodied. A central processing unit (CPU) 2402 is coupled to system bus 2404. The CPU 2402 may be any general-purpose CPU, although other types of architectures of CPU 2402 (or other components of exemplary system 2400) may be used as long as CPU 2402 (and other components of system 2400) supports the operations as described herein. Those of ordinary skill in the art will appreciate that, while only a single CPU 2402 is shown in FIG. 19, additional CPUs may be present. Moreover, the system 2400 may comprise a networked, multi-processor or HPC computer system that may include a hybrid parallel CPU/GPU system and may be housed at a location that is far from that where the data is collected. The CPU 2402 may execute the various logical instructions according to various teachings disclosed herein. For example, the CPU 2402 may execute machine-level instructions for performing processing according to the operational flow described.

The data analysis system 2400 may also include computer components such as non-transitory, computer-readable media. Examples of computer-readable media include a random access memory ("RAM") 2406, which may be SRAM, DRAM, SDRAM, or the like. The system 2400 may also include additional non-transitory, computer-readable media such as a read-only memory ("ROM") 2408, which may be PROM, EPROM, EEPROM, or the like. RAM 2406 and ROM 2408 hold user and system data and programs, as is known in the art. The system 2400 may also include an input/output (I/O) adapter 2410, a communications adapter 2422, a user interface adapter 2424, and a display adapter 2418.

The I/O adapter 2410 may connect additional non-transitory, computer-readable media such as a storage device(s) 2412, including, for example, a hard drive, a compact disc ("CD") drive, a floppy disk drive, a tape drive, and the like to data analysis system 2400. The storage device(s) may be used when RAM 2406 is insufficient for the memory requirements associated with storing data for operations of the present disclosure. The data storage of the system 2400 may be used for storing information and/or other data used or generated as disclosed herein. For example, storage device(s) 2412 may be used to store configuration information or additional plug-ins in accordance with the present disclosure. Further, user interface adapter 2424 couples user input devices, such as a keyboard 2428, a pointing device 2426 and/or output devices to the system 2400. The display adapter 2418 is driven by the CPU 2402 to control the display on a display device 2420 to, for example, present information to the user regarding available plug-ins.

The architecture of data analysis system 2400 may be varied as desired. For example, any suitable processor-based device may be used, including without limitation personal computers, laptop computers, computer workstations, and multi-processor servers. Moreover, embodiments of the present disclosure may be implemented on application specific integrated circuits ("ASICs") or very large scale integrated ("VLSI") circuits. In fact, persons of ordinary skill in the art may use any number of suitable hardware structures capable of executing logical operations according to embodiments of the present disclosure. The term "processing circuit" encompasses a hardware processor (such as those found in the hardware devices noted above), ASICs, and VLSI circuits. Input data to the system 2400 may include various plug-ins and library files. Input data may additionally include configuration information.

In an embodiment, a method of examining a material includes disposing the material in a dielectric contrast analysis structure, wherein the dielectric contrast analysis structure includes a bulk dielectric substance; and a plurality of receptacles in the bulk dielectric substance, wherein the material is disposed in one or more of the plurality of receptacles; exposing the dielectric contrast analysis structure to incident electromagnetic radiation; detecting resultant electromagnetic radiation from the exposed dielectric contrast analysis structure; and analyzing the detected resultant electromagnetic radiation to estimate at least one of a phase fraction and a phase distribution in the material.

In one or more embodiments disclosed herein, the analyzing includes at least one of: estimating at least one of a complex dielectric constant of the material, a complex permittivity of the material, a complex conductivity of the material, and a complex index of refraction of the material;

processing the detected resultant electromagnetic radiation to extract relevant low frequency information; and averaging the detected resultant electromagnetic radiation over a range of orientations to improve signal-to-noise.

In one or more embodiments disclosed herein, the detecting includes measuring a first transmission coefficient of the resultant electromagnetic radiation through the dielectric contrast analysis structure along a first axis; and measuring a second transmission coefficient of the resultant electromagnetic radiation through the dielectric contrast analysis structure along a second axis, different from the first axis; and the analyzing includes comparing the first transmission coefficient and the second transmission coefficient.

In one or more embodiments disclosed herein, the incident electromagnetic radiation comprises a plurality of frequencies; and the comparing comprises plotting the first and second transmission coefficient measurements as functions of the plurality of frequencies and of an orientation of the first axis with respect to the second axis.

In one or more embodiments disclosed herein, the method also includes measuring a plurality of transmission coefficients of the resultant electromagnetic radiation through the dielectric contrast analysis structure along a plurality of axes or orientations, each of the plurality of axes coplanar with the first axis and the second axis.

In one or more embodiments disclosed herein, the first axis, the second axis, and the plurality of axes are distributed symmetrically across a 360° arc.

In one or more embodiments disclosed herein, the incident electromagnetic radiation comprises a plurality of frequencies; the comparing comprises creating plots of the first, second, and plurality of transmission coefficient measurements as functions of the plurality of frequencies and of relative orientations of the first axis, the second axis, and the plurality of axes; and the analyzing further comprises statistically evaluating the data and/or plots.

In one or more embodiments disclosed herein, the analyzing further comprises using effective medium theory to determine an index of refraction for each transmission coefficient measurement.

In one or more embodiments disclosed herein, the method also includes estimating, based on the determined indices of refraction, fractions of one or more substances in the material.

In one or more embodiments disclosed herein, the incident electromagnetic radiation comprises one or more frequencies between 1 megahertz and 100 gigahertz.

In one or more embodiments disclosed herein, the disposing the material in the dielectric contrast analysis structure comprises flowing the material through at least a subset of the plurality of receptacles.

In one or more embodiments disclosed herein, the method also includes repeating the exposing, detecting, and analyzing steps as the material flows through at least the subset of the plurality of receptacles.

In an embodiment, a system for examining a material includes an electromagnetic radiation source; a dielectric contrast analysis structure including a bulk dielectric substance; and a plurality of receptacles in the bulk dielectric substance for receiving the material; and an electromagnetic radiation detector, wherein the dielectric contrast analysis structure is between the electromagnetic radiation source and the electromagnetic radiation detector.

In one or more embodiments disclosed herein, each of the plurality of receptacles is a generally elongated structure; the plurality of receptacles are generally parallel with one another; and the plurality of receptacles are generally perpendicular to a path between the electromagnetic radiation source and the electromagnetic radiation detector.

In one or more embodiments disclosed herein, at least one of the plurality of receptacles is generally cylindrical.

In one or more embodiments disclosed herein, each of at least of subset of the plurality of receptacles includes a generally elongated structure; and openings at each end of the generally elongated structure providing a flow path for the material.

In one or more embodiments disclosed herein, the bulk dielectric substance comprises at least one of a polyethylene, a polycarbonate, a ceramic, and any combination thereof.

In one or more embodiments disclosed herein, the electromagnetic radiation source and the electromagnetic radiation detector define a primary axis therebetween; and the electromagnetic radiation detector is capable of detecting resultant radiation from the dielectric contrast analysis structure along at least one axis offset from the primary axis.

In one or more embodiments disclosed herein, the electromagnetic radiation detector is capable of simultaneously detecting resultant radiation from the dielectric contrast analysis structure along a plurality of axes coplanar to the primary axis.

In one or more embodiments disclosed herein, the system also includes a spectral analyzer coupled to the electromagnetic radiation detector.

In one or more embodiments disclosed herein, the system also includes a rotation actuator coupled to at least one of the electromagnetic radiation source, the electromagnetic radiation detector, and the dielectric contrast analysis structure, and capable of actuating relative rotation/orientation between the dielectric contrast analysis structure and the at least one of the electromagnetic radiation source and the electromagnetic radiation detector.

In one or more embodiments disclosed herein, the system also includes a controller coupled to the electromagnetic radiation source, the electromagnetic radiation detector, and the rotation actuator, and capable of correlating measurements of detected resultant radiation with at least one of a frequency of incident radiation from the electromagnetic radiation source and an orientation of the detected resultant radiation relative to the incident radiation.

Further embodiments include:

A. A method of examining a material, the method comprising: disposing the material in a dielectric contrast analysis structure, wherein the dielectric contrast analysis structure comprises: a bulk dielectric substance; and a plurality of receptacles in the bulk dielectric substance, wherein the material is disposed in one or more of the plurality of receptacles; exposing the dielectric contrast analysis structure to incident electromagnetic radiation; detecting resultant electromagnetic radiation from the exposed dielectric contrast analysis structure; and analyzing the detected resultant electromagnetic radiation to estimate at least one of a phase fraction and a phase distribution in the material.

B. The method of embodiment A, wherein the analyzing comprises at least one of: estimating at least one of a complex dielectric constant of the material, a complex permittivity of the material, a complex conductivity of the material, and a complex index of refraction of the material; processing the detected resultant electromagnetic radiation to extract relevant low frequency information; and averaging the detected resultant electromagnetic radiation over a range of orientations to improve signal-to-noise.

C. The method of embodiments A or B, wherein: the detecting comprises: measuring a first transmission coefficient of the resultant electromagnetic radiation through the dielectric contrast analysis structure along a first axis; and measuring a second transmission coefficient of the resultant electromagnetic radiation through the dielectric contrast analysis structure along a second axis, different from the first axis; and the analyzing comprises: comparing the first transmission coefficient and the second transmission coefficient.

D. The method of embodiment C, wherein: the incident electromagnetic radiation comprises a plurality of frequencies; and the comparing comprises plotting the first and second transmission coefficient measurements as functions of the plurality of frequencies and of an orientation of the first axis with respect to the second axis.

E. The method of embodiments C or D, further comprising measuring a plurality of transmission coefficients of the resultant electromagnetic radiation through the dielectric contrast analysis structure along a plurality of axes, each of the plurality of axes coplanar with the first axis and the second axis.

F. The method of embodiment E, wherein the first axis, the second axis, and the plurality of axes are distributed symmetrically across a 360° arc.

G. The method of embodiments E or F, wherein: the incident electromagnetic radiation comprises a plurality of frequencies; the comparing comprises creating plots of the first, second, and plurality of transmission coefficient measurements as functions of the plurality of frequencies and of relative orientations of the first axis, the second axis, and the plurality of axes; and the analyzing further comprises statistically evaluating the data and/or plots.

H. The method of any of the embodiments C-G, wherein the analyzing further comprises using effective medium theory to determine an index of refraction for each transmission coefficient measurement.

I. The method of any of the embodiments C-H, further comprising estimating, based on the determined indices of refraction, fractions of one or more substances in the material. J. The method of any of the embodiments A-I, wherein the analyzing further comprises using one or more machine learning methods to build training models from transmission coefficient measurements.

K. The method of embodiment J, further comprising estimating, based on the determined machine learning training models, fractions of one or more substances in the material.

L. The method of embodiment K, wherein the machine learning methods include, but are not limited to, Monte Carlo cross-validation method, k-Nearest Neighbor method, Support Vector Machine method, Random Forests method, and any Deep Learning methods such as Artificial Neural Network and Convolutional Neural Network.

M. The method of any preceding embodiment, wherein the incident electromagnetic radiation comprises one or more frequencies between 1 megahertz and 100 gigahertz.

N. The method of any preceding embodiment, wherein the disposing the material in the dielectric contrast analysis structure comprises flowing the material through at least a subset of the plurality of receptacles.

O. The method of embodiment N, further comprising repeating the exposing, detecting, and analyzing steps as the material flows through at least the subset of the plurality of receptacles.

P. A system for examining a material, the system comprising: an electromagnetic radiation source; a dielectric contrast analysis structure comprising: a bulk dielectric substance; and a plurality of receptacles in the bulk dielectric substance for receiving the material; and an electromagnetic radiation detector, wherein the dielectric contrast analysis structure is between the electromagnetic radiation source and the electromagnetic radiation detector.

Q. The system of embodiment P, wherein: each of the plurality of receptacles is a generally elongated structure; the plurality of receptacles are generally parallel with one another; and the plurality of receptacles are generally perpendicular to a path between the electromagnetic radiation source and the electromagnetic radiation detector.

R. The system of embodiments P or Q, wherein at least one of the plurality of receptacles is generally cylindrical.

S. The system of any of the embodiments P-R, wherein each of at least of subset of the plurality of receptacles comprises: a generally elongated structure; and openings at each end of the generally elongated structure providing a flow path for the material.

T. The system of any of the embodiments P-S, wherein the bulk dielectric substance comprise one or more materials having a relative dielectric permittivity within the range from about 1.0 to about 100.

U. The system of any of the embodiments P-T, wherein the bulk dielectric substance comprises at least one of a polyethylene, a polycarbonate, a ceramic, and any combination thereof.

V. The system of any of the embodiments P-U, wherein: the electromagnetic radiation source and the electromagnetic radiation detector define a primary axis therebetween; and the electromagnetic radiation detector is capable of detecting resultant radiation from the dielectric contrast analysis structure along at least one axis offset from the primary axis.

W. The system of embodiment V, wherein the electromagnetic radiation detector is capable of simultaneously detecting resultant radiation from the dielectric contrast analysis structure along a plurality of axes coplanar to the primary axis.

X. The system of any of the embodiments P-W, further comprising a spectral analyzer coupled to the electromagnetic radiation detector.

Y. The system of any of the embodiments P-X, further comprising a rotation actuator coupled to at least one of the electromagnetic radiation source, the electromagnetic radiation detector, and the dielectric contrast analysis structure, and capable of actuating relative rotation between the dielectric contrast analysis structure and the at least one of the electromagnetic radiation source and the electromagnetic radiation detector.

Z. The system of embodiment Y, further comprising a controller coupled to the electromagnetic radiation source, the electromagnetic radiation detector, and the rotation actuator, and capable of correlating measurements of detected resultant radiation with at least one of a frequency of incident radiation from the electromagnetic radiation source and an orientation of the detected resultant radiation relative to the incident radiation.

The foregoing description is directed to particular example embodiments of the present disclosure. It will be apparent, however, to one skilled in the art, that many modifications and variations to the embodiments described herein are possible. All such modifications and variations are intended to be within the scope of the present disclosure, as defined in the appended claims.

The invention claimed is:

1. A method of examining a material comprising fluid, the method comprising:
   flowing the material through a plurality of receptacles, wherein the plurality of receptacles are substantially parallel with one another, wherein the plurality of receptacles are disposed in a dielectric contrast analysis structure that is disposed in a pipe, and wherein the dielectric contrast analysis structure comprises: a bulk dielectric substance having a first end, a second end, and the plurality of receptacles disposed within the bulk dielectric substance, the receptacles having a first end disposed toward the first end of the bulk dielectric substance and a second end disposed toward the second end of the bulk dielectric substance, wherein a flow path of the material through the receptacles is from the first end of the bulk dielectric substance to the second end of the bulk dielectric substance;

exposing an outer surface of the dielectric contrast analysis structure and the material while in the plurality of receptacles to incident electromagnetic radiation at an angle substantially perpendicular to the flow path;

detecting resultant electromagnetic radiation from the exposed dielectric contrast analysis structure, wherein a dielectric constant of a material of the bulk dielectric substance provides contrast with a dielectric constant for the material flowing through the plurality of receptacles, wherein a path taken by the incident electromagnetic radiation through the dielectric contrast analysis structure is affected by interactions at interfaces of dielectric discontinuity; and analyzing the detected resultant electromagnetic radiation to estimate at least one of a phase fraction and a phase distribution in the material.

2. The method of claim 1, wherein the analyzing comprises: estimating at least one of a complex dielectric constant of the material, a complex permittivity of the material, a complex conductivity of the material, and a complex index of refraction of the material; processing the detected resultant electromagnetic radiation to extract relevant low frequency information; or averaging the detected resultant electromagnetic radiation over a range of orientations to improve signal-to-noise.

3. The method of claim 1, wherein: the detecting comprises:

measuring a first transmission coefficient of a plurality of transmission coefficient of the resultant electromagnetic radiation through the dielectric contrast analysis structure along a first axis; and measuring a second transmission coefficient of the plurality of transmission coefficient of the resultant electromagnetic radiation through the dielectric contrast analysis structure along a second axis, different from the first axis; wherein the analyzing comprises: comparing the first transmission coefficient and the second transmission coefficient.

4. The method of claim 3, wherein: the incident electromagnetic radiation comprises a plurality of frequencies; and the comparing comprises plotting the first and second transmission coefficient measurements as functions of the plurality of frequencies and of a relative orientation of the first axis with respect to the second axis.

5. The method of claim 3, further comprising measuring the plurality of transmission coefficients of the resultant electromagnetic radiation through the dielectric contrast analysis structure along a plurality of axes, each of the plurality of axes coplanar with the first axis and the second axis.

6. The method of claim 5, wherein the first axis, the second axis, and the plurality of axes are distributed symmetrically across a 360° arc.

7. The method of claim 3 wherein:
the incident electromagnetic radiation comprises a plurality of frequencies;
the comparing comprises creating plots of the first, second, and plurality of transmission coefficient measurements as functions of the plurality of frequencies and of relative orientations of the first axis, the second axis, and a plurality of axes; wherein the analyzing further comprises statistically evaluating the plots.

8. The method of claim 7, wherein the plots have 2-fold symmetry or a 4-fold symmetry.

9. The method of claim 3, wherein the analyzing further comprises using effective medium theory to determine an index of refraction for each transmission coefficient measurement.

10. The method of claim 9, further comprising estimating, based on the determined indices of refraction, fractions of one or more substances in the material.

11. The method of claim 1, wherein the incident electromagnetic radiation comprises one or more frequencies between 1 megahertz and 100 gigahertz.

12. The method of claim 1, further comprising repeating the exposing, detecting, and analyzing steps as the material flows through at least a subset of the plurality of receptacles.

13. The method of claim 1 wherein: each of the receptacles of the plurality of receptacles is an elongated structure having an opening at the first end of the receptacle and an elongated side substantially perpendicular to the first end of the receptacle; and the incident electromagnetic radiation has a path substantially perpendicular to the elongated side of each of the receptacles of the plurality of receptacles.

14. The method of claim 1 further comprising rotating the dielectric contrast analysis structure along an axis disposed through the first end and the second end of the bulk dielectric substance.

15. The method of claim 14, wherein rotating the dielectric contrast analysis structure is performed while exposing the material in the plurality of receptacles to the incident electromagnetic radiation.

16. The method of claim 1, wherein each of the receptacles has a diameter from 10 mm to 2 cm.

17. The method of claim 16 wherein each of the receptacles has a spacing from an adjacent receptacle of the plurality of receptacles from 1 cm to 3 cm, as measured center diameter to center diameter.

18. The method of claim 1, wherein the bulk dielectric substance has a diameter from 15 cm to 25 cm.

19. The method of claim 1, wherein the plurality of receptacles comprises from 50 to 100 receptacles.

20. The method of claim 1, wherein a distance between the first end of the bulk dielectric substance and the second end of the bulk dielectric substance is from 10 cm to 20 cm.

21. The method of claim 1, wherein the pipe is a wellbore, a tubular within a wellbore, a wellhead, a surface pipeline, a subterranean pipeline, an ocean bottom pipeline, or a riser.

22. The method of claim 1, wherein the plurality of receptacles is a square array of receptacles.

* * * * *